United States Patent [19]

Scott et al.

[11] Patent Number: 5,734,086

[45] Date of Patent: Mar. 31, 1998

[54] CYTOCHROME P450$_{LPR}$ GENE AND ITS USES

[75] Inventors: Jeffrey G. Scott, Ithaca, N.Y.; Takashi Tomita, Omiya, Japan

[73] Assignee: Cornell Research Foundation, Inc., Ithaca, N.Y.

[21] Appl. No.: 457,274

[22] Filed: Jun. 1, 1995

Related U.S. Application Data

[62] Division of Ser. No. 241,388, May 10, 1994.

[51] Int. Cl.$^6$ .............................. A01H 1/06; A01H 4/00; C12N 15/00; C12N 15/82

[52] U.S. Cl. .................... 800/205; 435/172.3; 435/320.1; 935/64; 935/67; 536/23.1; 536/23.5

[58] Field of Search ...................... 800/205; 435/172.3, 435/320.1; 935/64, 67; 536/23.1, 23.5

[56] References Cited

U.S. PATENT DOCUMENTS

| | | |
|---|---|---|
| 4,766,068 | 8/1988 | Oeda et al. . |
| 5,164,313 | 11/1992 | Gelboin et al. . |
| 5,212,296 | 5/1993 | Dean et al. . |
| 5,364,787 | 11/1994 | Orser et al. . |

FOREIGN PATENT DOCUMENTS

| | | |
|---|---|---|
| 193259 | 9/1986 | European Pat. Off. . |

OTHER PUBLICATIONS

Meltzer, *Biochemistry, The Chemical Reactions of Living Cells*, Academic Press, pp. 1005–1006 (1977).

Mayer et al., "Purification and Characterization of NADPH–Cytochrome c (P450) Reductase from the House Fly," *Biological Abstracts*, Abstract No. 27154, 64(5):2666 (1977).

Feyereisen et al., "Isolation and Sequence of cDNA Encoding a Cytochrome P–450 from an Insecticide–Resistant Strain of the House Fly," *Proc. Natl. Acad. Sci. U.S.A.*, 86(5):1465–1469 (1989).

Potrykus, "Gene Transfer to Cereals: An Assessment," *Bio/Technology*, 8:535–542 (1990).

Koener et al., "The cDNA and Deduced Protein Sequence of House Fly NADPH–Cytochrome P450 Reductase," *Biological Abstracts*, Abstract No. 17435, 96(2): AB–595 (1993).

S. Kawano, et al., Purification of Human Liver Cytochrome P450 Catalyzing Testosterone 6β–Hydroxylation *J. Biochem.*, 102:493 (1987).

Golly, et al., "The Functional Role of Cytochrome b$_5$ Reincorporated into Hepatic Microsomal Fractions," *Arch. Biochem. Biophys.*, 260:232 (1988).

D.W. Nebert, et al., "The P450 Superfamily: Update on New Sequences, Gene Mapping and Recommended Nomenclature," *DNA Cell Biol.*, 10:1–14 (1991).

E. Hodgson, "The Significance of Cytochrome P450 in Insects," *Insect Biochem.*, 13:237–246 (1983).

D.R. Vincent, et al., "Cytochrome P450 in Insects. 6. Age Dependency and Phenobarbital Inducibility of Cytochrome P450 Reductase and Monooxygenase Activity in Susceptible and Resistant Strains of *Musca domestica*," *Pestic. Biochem. Physiol.* 23:171–81 (1985).

Eldefrawi, et al., "Methylenedioxyphenyl Derivatives as Synergists for Carbamate Insecticides in Susceptible, DDT–and Parathion–Resistant House Flies," *J. Econ. Entomol.*, 53:231–34 (1960).

G.P. Georghiou, et al., "The Absorption and Metabolism of 3–isopropyl–phenyl N–methylcarbamate by Susceptible and Carbamate–Selected Strains in House Flies," *J. Econ. Entomol.*, 54:231–33 (1961).

G.P. Georghiou, et al., "The Development and Characterization of Resistance to Carbamate Insecticides in the House Fly, *Musca domestica*," *J. Econ. Entomol.*, 54:132–140 (1961).

R.D. Schonbrod, et al., "Hydroxylation as a Factor in Resistance in House Flies and Blow Flies," *J. Econ. Entomol.*, 58:74–78 (1965).

M. Tsukamoto, et al., "Metabolism of Methylcarbamate Insecticides by the NADPH$_2$–requiring Enzyme System from Houseflies," *Nature London*, 213:49–51 (1967).

F.J. Oppenoorth, et al., "DDT Resistance in the Housefly Caused by Microsomal Degradation," *Ent. Exp. Appl.*, 11:81–93 (1968).

R.D. Schonbrod, et al., "Microsomal Oxidases in the House Fly: A Survey of Fourteen Strains," *Life Sci.*, 7:681–88 (1968).

M.D. Folsom, et al., "Biochemical Characteristics of Microsomal Preparations from Diazinon–resistant and Susceptible Houseflies," *Life Sci.*, 9:869–975 (1970).

L.B. Brattsten, et al., "Insecticide Resistance: Challenge to Pest Management and Basic Research," *Science*, 231:1255–60 (1986).

J.G. Scott, et al., "Mechanisms Responsible for High Levels of Permethrin Resistance in the House Fly," *Pestic. Sci.*, 17:195–206 (1986).

J.G.Scott, "Insecticide Resistance in Insects," *Handbook of Pest Management*, vol. 2, D. Pimentel, ed., CRC Press, Boca Raton, FL (1991).

(List continued on next page.)

*Primary Examiner*—Gary Benzion
*Attorney, Agent, or Firm*—Nixon, Hargrave, Devans & Doyle

[57] ABSTRACT

The present invention relates to an isolated DNA molecule encoding a cytochrome P450$_{lpr}$ polypeptide as well as the isolated cytochrome P450$_{lpr}$ polypeptide itself. The DNA molecule can be inserted as a heterologous DNA in an expression vector forming a recombinant DNA expression system for producing the polypeptide. Likewise, the heterologous DNA, usually inserted in an expression vector to form a recombinant DNA expression system, can be incorporated in a host cell to achieve this objective.

The DNA molecule of the present invention can be utilized for control of larval or adult insects, bioremediation of insecticides, and conferring pesticide resistance to crop plants.

18 Claims, 9 Drawing Sheets

OTHER PUBLICATIONS

C.F. Wilkinson, "Role of Mixed–function Oxidases in Insecticide Resistance," *Pest Resistance in Pesticides*, G.P. Georghiou and T. Saito, eds., Plenum Press, New York (1983).

C.W. Fisher, et al., "Partial Purification and Characterization of Phenobarbital–Induced House Fly P–450," *Arch. Insect Biochem. Physiol.*, 1:127–38 (1984).

R.D. Schonbrod, et al., "The Solubilization and Separation of Two Forms of Microsomal Cytochrome P–450 from the House Fly, *Musca domestica*," *Biochem. Biophys. Res. Comm.*, 64:829–833 (1975).

J. Capdeila, et al., "Multiple Forms of Housefly Cytochrome P–450," *Microsomes and Drug Oxidations*, V. Ulrich, ed., Pergamon Press, New York (1977).

S.J. Yu, et al., "Cytochrome P–450 in Insects. 1. Differences in the Forms Present in Insecticide Resistant and Susceptible House Flies," *Pestic. Biochem. Physiol.*, 12:239–48 (1979).

A.F. Moldenke, et al., "Cytochrome P–450 in Insects 4. Reconstitution of Cytochrome P–450–dependent Monooxygenase Activity in the House Fly," *Pestic. Biochem. Physiol.*, 21:358–67 (1984).

M.J.J. Ronis, et al., Characterization of Multiple Foms of Cytochrome P–450 From an Insecticide Resistant Strain of House *Pestic Biochem. Physiol.*,32:74–90 (1988).

G.D. Wheelock, et al., "Simultaneous Purification of a Cytochrome P–450 and Cytochrome $b_5$ from the House Fly *Musca domestica* L.", *Insect Biochem.*, 19:481–489 (1989).

J.G. Scott, et al., "Characterization of a Cytochrome P450 Responsible for Pyrethroid Resistance in the House Fly," *Molecular Basis of Insecticide Resistance: Diversity Among Insects*, Symposium Series 505, C.J. Mullin and J.G. Scott, eds., American Society, Washington, D.C. (1992).

G.D. Wheelock, et al., "Immunological Detection of Cytochrome P450 from Insecticide Resistant and Susceptible House Flies (*Musca domestica*)," *Pestic. Biochem. Physiol.*, 38:130–39 (1990).

G.D. Wheelock, et al., "Expression of Cytochrome P–450$_{lpr}$ is Developmentally Regulated and Limited to House Fly," *J. Biochem. Toxicol.*, 6:239–246 (1991).

M.E. McManus, et al., "Identification and Quantitation in Human Liver of Cytochrome P–450 Analogous to Rabbit Cytochrome P–450 Forms 4 and 6," *Xenobiotica*, 18:207–16 (1988).

S.S.T. Lee, et al., "Tissue Distribution of Microsomal Cytochrome P450 Monooxygenases and Their Inducibility by Phenobarbital the House Fly, *Musca domestica* L.," *Insect Bichem. Molec. Biol.*, 22:699–711 (1992).

G.D. Wheelock, et al., "Anti–P450$_{lpr}$ Antiserum Inhibits Specific Monooxygenase Activities in LPR House Fly Microsome," *The Journal of Experimental Zoology*, 264:153–58 (1992).

G.D. Wheelock, et al., "The Role of Cytochrome P450$_{lpr}$ in Deltamethrin Metabolism by Pyrethroid–Resistant and Susceptible Strains of House Flies," *Pest. Biochem. & Physiol.*, 43:67–77 (1992).

S.S.T. Lee, et al., "In Vitro Induction of Microsomal Cytochrome P–450 Monooxygenases by Phenobarbital in Fat Bodies of Adult House Fly, *Musca domestica* L.," *Insect Biochem. Molec. Biol.*, 22(7):691–98 (1992).

R. Hatano, et al., "Anti–P450$_{lpr}$ Antiserum Inhibits the Activation of Chlorpyrifos to Chlorpyrifos Oxan in House Fly Microsmes," *Pestic. Biochem. & Physiol.*, 45:228–33 (1993).

J.G. Scott., "The Cytochrome P450 Microsomal Monooxygenases of Insects: Recent Advances," *Rev. Pestic. Toxicol.*, vol. 2, R.M. Roe, et al., editors (1993).

J.G. Scott, et al. "Purification and Characterization of a Cytochrome P–450 From Insecticde Susceptible and Resistant Strains at Housefly *Musca domestica* L., Before and After Phenobarbital Exposure," *Arch. Insect Biochem. & Physiol.*, 24:1–19 (1993).

```
LPR allelle    1 MLLLLLLIVVTTLYIFAKLHYTKWERLGFESDKATIPLGSMAKVFHKERP  50
CS allelle       ||||||||||||||||||||||||||||||||||||||||||||||||||
               1 MLLLLLLIVVTTLYIFAKLHYTKWERLGFESDKATIPLGSMAKVFHKERP  50

51 FGLVMSDIYDKCHEKVVGIYLFFKPALLVRDAELARQILTTDFNSFHDRG 100
                 ||||||||||||||||||||||||||||||||||||||||||||||||||
              51 FGLVMSDIYDKCHEKVVGIYLFFKPALLVRDAELARQILTTDFNSFHDRG 100

101 LYVDEKNDPMSANLFVMEGQSWRTLRMKLAPSFSSGKLKGMFETVDDVAD 150
                 ||||||||||||||||||||||||||||||||||||||||||||||||||
             101 LYVDEKNDPMSANLFVMEGQSWRTLRMKLAPSFSSGKLKGMFETVDDVAD 150

151 KLINHLNERLKDGQTHVLEIKSILTTYAVDIIGSVIFGLEIDSFTHPDNE 200
                 ||||||||||||||||||||||||||||||||||||||||||||||||||
             151 KLINHLNERLKDGQTHVLEIKSILTTYAVDIIGSVIFGLEIDSFTHPDNE 200

201 FRVLSDRLFNPKKSTMLERHRNLSTFMCPPLAKLLSRLGAKDPITYRLRD 250
                 |||||||||||||||||||| |||||||||||||||||||||||||||||
             201 FRVLSDRLFNPKKSTMLERFRNLSTFMCPPLAKLLSRLGAKDPITYRLRD 250

251 IVKRTIEFREEKGVVRKDLLQLFIQLRNTGKISDDNDKLWHDVESTAENL 300
                 ||||||||||||||||||||||||||||||||||||||||||||||||||
             251 IVKRTIEFREEKGVVRKDLLQLFIQLRNTGKISDDNDKLWHDVESTAENL 300

301 KAMSIDMIASNSFLFYIAGSETTAATTSFTIYELAMYPEILKKAQSEVDE 350
                 ||||||||||||||||||||||||||||||||||||||||||||||||||
             301 KAMSIDMIASNSFLFYIAGSETTAATTSFTIYELAMYPEILKKAQSEVDE 350

351 CLQRHGLKPQGRLTYEAIQDMKYLDLCVMETTRKYPGLPFLNRKCTQDFQ 400
                 ||||||||||||||||||||||||||||||||||||||||||||||||||
             351 CLQRHGLKPQGRLTYEAIQDMKYLDLCVMETTRKYPGLPFLNRKCTQDFQ 400

401 VPDTKLTIPKETGIIISLLGIHRDPQYFPQPEDYRPERFADESKDYDPAA 450
                 ||||||||||||||||||||||||||||||||||||||||||||||||||
             401 VPDTKLTIPKETGIIISLLGIHRDPQY*PQPEDYRPERFADESKDYDPAA 450

451 YMPFGEGPRHCIAQRMGVINSKVALAKILANFNIQPMPRQEVEFKFHSAP 500
                 ||||||||||||||||| |||||||||||||||||||||||||||||||
             451 YMPFGEGPRHCIAQRMGVMNSKVALAKILANFNIQPMPRQEVEFKFHSAP 500

501 VLVPVNGLNVGLSKRW* 517
                 |||||||||||||||||
             501 VLVPVNGLNVGLSKRW* 517
```

```
LPR allele  ..gacagggagaaggaaatgataagaaatgtgcaaagttttacatgcattcgaatcattctgttt
CS allele LPR allele  cacaaaatgaccggcaactattcagttgttaatgtaacacgtacccgattagatcggaaatattt
CS allele LPR allele  tgtaacgttagtgaatagctaggagaaaattgcaaaactaaaATGTTGTTATTACTGCTGCTGA
CS allele                                                                A TTGTGGTGACGACCCTCTATATCTTTGCCAAACTCCATTATACGAAATGGGAACGTTTGGGTTTC
                                  C                     T GAATCGGATAAGGCCACCATACCCCTGGGCTCAATGGCAAAGGTATTCCACAAGGAACGGCCATT
                                               A G                G TGGCCTGGTTATGTCCGACATATATGACAAATGCCACGAGAAGGTTGGTGGGCATTTATTTGTTCT
                                   A     C TCAAGCCGGCCCTACTGGTACGTGATGCCGAATTGGCCGAGACAAATTTTGACCACGGATTTTAAT
                                 G    C AGCTTCCACGATCGTGGCCCTCTATGTGGATGAGAAAAATGATCCAATGTCGGGCGAATCTTTTCGT
                                 T
```

GATGGAGGGTCAATCATGGCGTACGCTGAGAATGAAATTGGCCCCCTCGTTTTCGTCGGGTAAAC

TCAAGGGGATGTTCGAAACGGTCGATGATGTGGCGGATAAATTAATAAATCACTTGAATGAGCGC

TTGAAGGATGGCCAGACGCCATGTTTTTGAAATCAAGAGTATTTTGACCACgtaagtactcatcgt
                                                                             Intron A tgagagaatttgtaagaagttttgaatttttactttaataaatgttcttcttcccccagCTATGC Intron A (continued)
TGTCGACATCATTGGTTCGGGTTCGGTGATATTCGGCCTGGAAATCGATAGTTTCACCCATCCGGACAATG AATTTCGTGTCTTAAGTGATCGTCTATTTAACCCAAAGAAGTCGACAATGTTGGAGAGAATTCGC
                                  G

AATTTATCAACCTTTATGTGTCCACCACTTGCCAAACTCTTGTGCGCCTTGGTGCCAAGGATCC

GATAACATATCGCCTGCCGCGACATCGTGAAACGGACGATAGAATTCGCGAAGAAAAGGGGCGTTG

TACGCAAAGATCTCTCCAGCTATTTATACAACTCAGAAATACTGGAAAAATTTCCGATGACAAT
                                                T
C

FIGURE 6B

```
GACAAGCTATGGCATGACGTTGAGTCGACGGGCGGGAAAATCTCAAAGCCATGTCTATCGATATGAT
                                                            C

TGCCTCCAATTCATTCCTATTCTATATTGCCGGTTCGGAAACAACGGGCCACAACATCATTTA
              T                         A

CCATCTATGAATTGGCCATGTATCCGGAAATTTTGAAAAAGGCCCAATCTGAGGTGGATGAGTGC
                                  C   G    AGC                T

CTGCAAAGGCATGGTCTCAAGCCCGCAGGGACGGGCTGACATATGAGGCAATACAGGATATGAAATA
      C                                  C     C

TTTGGATTTGTGTGTTATGGgtaagagggaaatttgaaattgtttttttatttttctaat
                    Intron B tattgcatgtttttgttgtagAACCACCCGCAAATACCCGGCCTGCCGTTTTGAATCGCAAA
Intron B (continued)                  T TGCACTCAGGATTCCAAGTACCCGACACAAAACTGACCATACCAAAGGAAACGGGAATTATCAT
                              T          C

CTCCTTGTTGGGCATCCATAGAGACCCACAGTATTCCCCCAACCCGAGGATTATAGGCCAGAAC
 C C

GCTTTGCCGATGAGAGCAAGGATTATGATCCAGCGGCATATATGCCTTTTGGAGAGGGTCCAAGG
```

FIGURE 6C

```
CATTGTATTGgtgagatgttgaaggggaggttcattaaatgtgaatattaatttgtattt
         C                       Intron C
tttccacacgTCAACGCATGGGCGTTATCAATTCCAAGGTAGCCTTGGCCAAAATATTGGCCA
                                  G
Intron C (continued)

ATTTTAATATTCAACCAATGCCCCGCCAAGAAGTTGAGTTCAAATTCCATTCAGCTCCTGTTCTG

GTGCCAGTAAATGGTCTCAATGTGGGCCCTGTCGAAGAGGTGGTGAagagcaagtggttaagtgaa
                               T  A ttgaggagtgcttttcgagatatatgttggtgattaggttataacgattatttaagaaccagt atttaagctttaattttttattcaaattttgaaatattgaaattaaaataacatatgtaaat aaaatt???????????????
```

FIGURE 6D

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
      ( A ) LENGTH: 1551 base pairs
      ( B ) TYPE: nucleic acid
      ( C ) STRANDEDNESS: double
      ( D ) TOPOLOGY: linear ( i i ) MOLECULE TYPE: DNA (cDNA)

( i i i ) HYPOTHETICAL: NO ( i v ) ANTI-SENSE: NO ( v i ) ORIGINAL SOURCE:
      ( A ) ORGANISM: Musca domestica
      ( B ) STRAIN: Learn-PyR
      ( D ) DEVELOPMENTAL STAGE: Adult ( v i i i ) POSITION IN GENOME:
      ( A ) CHROMOSOME/SEGMENT: Chromosome 1

( x i ) SEQUENCE DESCRIPTION: SEQ ID NO: 1:

```
ATGTTGTTAT TACTGCTGCT GATTGTGGTG ACGACCCTCT ATATCTTTGC CAAACTCCAT    60
TATACGAAAT GGGAACGTTT GGGTTTCGAA TCGGATAAGG CCACCATACC CCTGGGCTCA   120
ATGGCAAAGG TATTCCACAA GGAACGGCCA TTTGGCCTGG TTATGTCCGA CATATATGAC   180
AAATGCCACG AGAAGGTGGT GGGCATTTAT TTGTTCTTCA AGCCGGCCCT ACTGGTACGT   240
GATGCCGAAT TGGCGAGACA AATTTTGACC ACGGATTTTA ATAGCTTCCA CGATCGTGGC   300
CTCTATGTGG ATGAGAAAAA TGATCCAATG TCGGCGAATC TTTTCGTGAT GGAGGGTCAA   360
TCATGGCGTA CGCTGAGAAT GAAATTGGCC CCCTCGTTTT CGTCGGGTAA ACTCAAGGGG   420
ATGTTCGAAA CGGTCGATGA TGTGGCGGAT AAATTAATAA ATCACTTGAA TGAGCGCTTG   480
AAGGATGGCC AGACGCATGT TTTGGAAATC AAGAGTATTT TGACCACCTA TGCTGTCGAC   540
ATCATTGGTT CGGTGATATT CGGCCTGGAA ATCGATAGTT TCACCCATCC GGACAATGAA   600
TTTCGTGTCT TAAGTGATCG TCTATTTAAC CCAAAGAAGT CGACAATGTT GGAGAGAATT   660
CGCAATTTAT CAACCTTTAT GTGTCCACCA CTTGCCAAAC TCTTGTCGCG CCTTGGTGCC   720
AAGGATCCGA TAACATATCG CCTGCGCGAC ATCGTGAAAC GGACGATAGA ATTTCGCGAA   780
GAAAAGGGCG TTGTACGCAA AGATCTTCTC CAGCTATTTA TACAACTCAG AAATACTGGA   840
AAAATTTCCG ATGACAATGA CAAGCTATGG CATGACGTTG AGTCGACGGC GGAAAATCTC   900
AAAGCCATGT CTATCGATAT GATTGCCTCC AATTCATTCC TATTCTATAT TGCCGGTTCG   960
GAAACAACGG CGGCCACAAC ATCATTTACC ATCTATGAAT TGGCCATGTA TCCGGAAATT  1020
TTGAAAAAGG CCCAATCTGA GGTGGATGAG TGCCTGCAAA GGCATGGTCT CAAGCCGCAG  1080
GGACGGCTGA CATATGAGGC AATACAGGAT ATGAAATATT TGGATTTGTG TGTTATGGAA  1140
ACCACCCGCA AATACCCCGG CCTGCCGTTT TTGAATCGCA AATGCACTCA GGATTTCCAA  1200
GTACCCGACA CAAAACTGAC CATACCAAAG GAAACGGGAA TTATCATCTC CTTGTTGGGC  1260
ATCCATAGAG ACCCACAGTA TTTCCCCCAA CCCGAGGATT ATAGGCCAGA ACGCTTTGCC  1320
GATGAGAGCA AGGATTATGA TCCAGCGGCA TATATGCCTT TTGGAGAGGG TCCAAGGCAT  1380
```

```
TGTATTGCTC  AACGCATGGG  CGTTATCAAT  TCCAAGGTAG  CCTTGGCCAA  AATATTGGCC    1440

AATTTTAATA  TTCAACCAAT  GCCCCGCCAA  GAAGTTGAGT  TCAAATTCCA  TTCAGCTCCT    1500

GTTCTGGTGC  CAGTAAATGG  TCTCAATGTG  GGCCTGTCGA  AGAGGTGGTG  A             1551
```

( 2 ) INFORMATION FOR SEQ ID NO:2:

( i ) SEQUENCE CHARACTERISTICS:
        ( A ) LENGTH: 517 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 2:

```
Met Leu Leu Leu Leu Leu Leu Ile Val Val Thr Thr Leu Tyr Ile Phe
 1               5                  10                  15

Ala Lys Leu His Tyr Thr Lys Trp Glu Arg Leu Gly Phe Glu Ser Asp
                20                  25                  30

Lys Ala Thr Ile Pro Leu Gly Ser Met Ala Lys Val Phe His Lys Glu
            35                  40                  45

Arg Pro Phe Gly Leu Val Met Ser Asp Ile Tyr Asp Lys Cys His Glu
        50                  55                  60

Lys Val Val Gly Ile Tyr Leu Phe Phe Lys Pro Ala Leu Leu Val Arg
 65                  70                  75                  80

Asp Ala Glu Leu Ala Arg Gln Ile Leu Thr Thr Asp Phe Asn Ser Phe
                85                  90                  95

His Asp Arg Gly Leu Tyr Val Asp Glu Lys Asn Asp Pro Met Ser Ala
            100                 105                 110

Asn Leu Phe Val Met Glu Gly Gln Ser Trp Arg Thr Leu Arg Met Lys
        115                 120                 125

Leu Ala Pro Ser Phe Ser Ser Gly Lys Leu Lys Gly Met Phe Glu Thr
    130                 135                 140

Val Asp Asp Val Ala Asp Lys Leu Ile Asn His Leu Asn Glu Arg Leu
145                 150                 155                 160

Lys Asp Gly Gln Thr His Val Leu Glu Ile Lys Ser Ile Leu Thr Thr
                165                 170                 175

Tyr Ala Val Asp Ile Ile Gly Ser Val Ile Phe Gly Leu Glu Ile Asp
            180                 185                 190

Ser Phe Thr His Pro Asp Asn Glu Phe Arg Val Leu Ser Asp Arg Leu
        195                 200                 205

Phe Asn Pro Lys Lys Ser Thr Met Leu Glu Arg Ile Arg Asn Leu Ser
    210                 215                 220

Thr Phe Met Cys Pro Pro Leu Ala Lys Leu Leu Ser Arg Leu Gly Ala
225                 230                 235                 240

Lys Asp Pro Ile Thr Tyr Arg Leu Arg Asp Ile Val Lys Arg Thr Ile
                245                 250                 255

Glu Phe Arg Glu Glu Lys Gly Val Val Arg Lys Asp Leu Leu Gln Leu
            260                 265                 270

Phe Ile Gln Leu Arg Asn Thr Gly Lys Ile Ser Asp Asp Asn Asp Lys
        275                 280                 285

Leu Trp His Asp Val Glu Ser Thr Ala Glu Asn Leu Lys Ala Met Ser
    290                 295                 300

Ile Asp Met Ile Ala Ser Asn Ser Phe Leu Phe Tyr Ile Ala Gly Ser
305                 310                 315                 320
```

```
         Glu  Thr  Thr  Ala  Ala  Thr  Thr  Ser  Phe  Thr  Ile  Tyr  Glu  Leu  Ala  Met
                             325                 330                           335

Tyr  Pro  Glu  Ile  Leu  Lys  Lys  Ala  Gln  Ser  Glu  Val  Asp  Glu  Cys  Leu
                        340                 345                      350

Gln  Arg  His  Gly  Leu  Lys  Pro  Gln  Gly  Arg  Leu  Thr  Tyr  Glu  Ala  Ile
                   355                           360                 365

Gln  Asp  Met  Lys  Tyr  Leu  Asp  Leu  Cys  Val  Met  Glu  Thr  Thr  Arg  Lys
              370                      375                      380

Tyr  Pro  Gly  Leu  Pro  Phe  Leu  Asn  Arg  Lys  Cys  Thr  Gln  Asp  Phe  Gln
         385                           390                 395                      400

Val  Pro  Asp  Thr  Lys  Leu  Thr  Ile  Pro  Lys  Glu  Thr  Gly  Ile  Ile  Ile
                             405                      410                      415

Ser  Leu  Leu  Gly  Ile  His  Arg  Asp  Pro  Gln  Tyr  Phe  Pro  Gln  Pro  Glu
                        420                      425                 430

Asp  Tyr  Arg  Pro  Glu  Arg  Phe  Ala  Asp  Glu  Ser  Lys  Asp  Tyr  Asp  Pro
                   435                      440                 445

Ala  Ala  Tyr  Met  Pro  Phe  Gly  Glu  Gly  Pro  Arg  His  Cys  Ile  Ala  Gln
              450                      455                      460

Arg  Met  Gly  Val  Ile  Asn  Ser  Lys  Val  Ala  Leu  Ala  Lys  Ile  Leu  Ala
         465                      470                      475                      480

Asn  Phe  Asn  Ile  Gln  Pro  Met  Pro  Arg  Gln  Glu  Val  Glu  Phe  Lys  Phe
                             485                      490                      495

His  Ser  Ala  Pro  Val  Leu  Val  Pro  Val  Asn  Gly  Leu  Asn  Val  Gly  Leu
                        500                      505                      510

Ser  Lys  Arg  Trp  Xaa
                        515
```

( 2 ) INFORMATION FOR SEQ ID NO:3:

( i ) SEQUENCE CHARACTERISTICS:
       ( A ) LENGTH: 19 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO: 3:

```
         Met  Leu  Leu  Leu  Leu  Leu  Leu  Ile  Val  Val  Thr  Thr  Leu  Tyr  Ile  Phe
         1                   5                        10                           15

Ala  Lys  Leu
```

( 2 ) INFORMATION FOR SEQ ID NO:4:

( i ) SEQUENCE CHARACTERISTICS:
       ( A ) LENGTH: 21 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO: 4:

```
         Gly  Leu  Tyr  Val  Asp  Glu  Lys  Asn  Asp  Pro  Met  Ser  Ala  Asn  Leu  Phe
         1                   5                        10                           15

Val  Met  Glu  Gly  Gln
                        20
```

( 2 ) INFORMATION FOR SEQ ID NO:5:

( i ) SEQUENCE CHARACTERISTICS:

(A) LENGTH: 6 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 5:

Asp  Asp  Asn  Asp  Lys  Leu
        1                  5

(2) INFORMATION FOR SEQ ID NO:6:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 6:

Glu  Thr  Gly  Ile  Ile  Ile  Ser  Leu  Leu  Gly  Ile  His
        1                  5                       10

(2) INFORMATION FOR SEQ ID NO:7:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 7:

Pro  Gln  Tyr  Phe  Pro  Gln  Pro  Glu  Asp  Tyr  Arg  Pro  Glu
        1                  5                       10

(2) INFORMATION FOR SEQ ID NO:8:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 8:

ACCGTCTGCT ATCATTCTTT CGCCAA                                                    26

(2) INFORMATION FOR SEQ ID NO:9:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 9:

TCTGAGCCTC TCCATCATGA CAGAA                                                     25

(2) INFORMATION FOR SEQ ID NO:10:

(i) SEQUENCE CHARACTERISTICS:
            (A) LENGTH: 29 base pairs
            (B) TYPE: nucleic acid (C) STRANDEDNESS: single
(D) TOPOLOGY: linear (ii) MOLECULE TYPE: DNA (xi) SEQUENCE DESCRIPTION: SEQ ID NO: 10:

TCATCGGTCT GCTAGGGAGA AAGTATCTG                29

(2) INFORMATION FOR SEQ ID NO:11:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 11:

TAATACGACT CACTATAGGG AGA                      23

(2) INFORMATION FOR SEQ ID NO:12:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 12:

TAATACGACT CACTATAGGG AGATTTTTTT TTTTTTTT      39

(2) INFORMATION FOR SEQ ID NO:13:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 13:

Thr Leu Tyr Ile Phe Ala Lys
 1               5

(2) INFORMATION FOR SEQ ID NO:14:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (vi) ORIGINAL SOURCE:
(A) ORGANISM: Musca domestica
(B) STRAIN: Learn-PyR
(D) DEVELOPMENTAL STAGE: Adult (viii) POSITION IN GENOME:
(A) CHROMOSOME/SEGMENT: Chromosome 1

(xi) SEQUENCE DESCRIPTION: SEQ ID NO: 14:

```
        Phe  Val  Met  Glu  Gly  Gln
        1              5
```

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Musca domestica
        ( B ) STRAIN: Learn-PyR
        ( D ) DEVELOPMENTAL STAGE: Adult ( v i i i ) POSITION IN GENOME:
        ( A ) CHROMOSOME/SEGMENT: Chromosome 1

( x i ) SEQUENCE DESCRIPTION: SEQ ID NO: 15:

```
        Gln  Tyr  Phe  Pro  Gln  Pro
        1              5
```

( 2 ) INFORMATION FOR SEQ ID NO:16:

( i ) SEQUENCE CHARACTERISTICS:
        ( A ) LENGTH: 2 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Musca domestica
        ( B ) STRAIN: Learn-PyR
        ( D ) DEVELOPMENTAL STAGE: Adult ( v i i i ) POSITION IN GENOME:
        ( A ) CHROMOSOME/SEGMENT: Chromosome 1

( x i ) SEQUENCE DESCRIPTION: SEQ ID NO: 16:

```
AA                                                                2
```

( 2 ) INFORMATION FOR SEQ ID NO:17:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Musca domestica
        ( B ) STRAIN: Learn-PyR
        ( D ) DEVELOPMENTAL STAGE: Adult ( v i i i ) POSITION IN GENOME:
        ( A ) CHROMOSOME/SEGMENT: Chromosome 1

( x i ) SEQUENCE DESCRIPTION: SEQ ID NO: 17:

AAAAA                                                                                                                                                                5

( 2 ) INFORMATION FOR SEQ ID NO:18:

( i ) SEQUENCE CHARACTERISTICS:
        ( A ) LENGTH: 74 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Musca domestica
        ( B ) STRAIN: Learn-PyR
        ( D ) DEVELOPMENTAL STAGE: Adult ( v i i i ) POSITION IN GENOME:
        ( A ) CHROMOSOME/SEGMENT: Chromosome 1

( x i ) SEQUENCE DESCRIPTION: SEQ ID NO: 18:

GTAAGTACTC ATCGTTGAGA GAATTGTAAG AAGTTTTGAA TTTTACTTTT AATAAAATGT      60

TCTTCTTCCC CCAG                                                        74

( 2 ) INFORMATION FOR SEQ ID NO:19:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Musca domestica
        ( B ) STRAIN: Learn-PyR
        ( D ) DEVELOPMENTAL STAGE: Adult ( v i i i ) POSITION IN GENOME:
        ( A ) CHROMOSOME/SEGMENT: Chromosome 1

( x i ) SEQUENCE DESCRIPTION: SEQ ID NO: 19:

GTAAGAGGGG AAATTTGAA ATTGTTTTTT TTTTATTTT CTAATTATTG CATGTTTTG         60

TTGTAG                                                                 66

( 2 ) INFORMATION FOR SEQ ID NO:20:

( i ) SEQUENCE CHARACTERISTICS:
        ( A ) LENGTH: 64 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Musca domestica (B) STRAIN: Learn-PyR
(D) DEVELOPMENTAL STAGE: Adult (viii) POSITION IN GENOME:
(A) CHROMOSOME/SEGMENT: Chromosome 1

(xi) SEQUENCE DESCRIPTION: SEQ ID NO: 20:

```
GTGAGATGTT GAAAGGGGAG CTTCATTAAA TTCTGAATAT TAATTTGTA TTTTTTTCC    60
ACAG                                                               64
```

(2) INFORMATION FOR SEQ ID NO:21:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (vi) ORIGINAL SOURCE:
(A) ORGANISM: Musca domestica
(B) STRAIN: Learn-PyR
(D) DEVELOPMENTAL STAGE: Adult (viii) POSITION IN GENOME:
(A) CHROMOSOME/SEGMENT: Chromosome 1

(xi) SEQUENCE DESCRIPTION: SEQ ID NO: 21:

```
Phe Xaa Xaa Gly Xaa Xaa Xaa Cys
1               5
```

(2) INFORMATION FOR SEQ ID NO:22:

(i) SEQUENCE CHARACTERISTICS:
(A) LENGTH: 507 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (vi) ORIGINAL SOURCE:
(A) ORGANISM: Musca domestica
(B) STRAIN: Rutgers
(D) DEVELOPMENTAL STAGE: Adult (viii) POSITION IN GENOME:
(A) CHROMOSOME/SEGMENT: Chromosome 5

(xi) SEQUENCE DESCRIPTION: SEQ ID NO: 22:

```
Met Asp Phe Gly Ser Phe Leu Leu Tyr Ala Leu Gly Val Leu Ala Ser
1               5                   10                  15

Leu Ala Leu Tyr Phe Val Arg Trp Asn Phe Gly Tyr Trp Lys Arg Arg
                20                  25                  30

Gly Ile Pro His Glu Glu Pro His Leu Val Met Gly Asn Val Lys Gly
                35                  40                  45

Leu Arg Ser Lys Tyr His Ile Gly Glu Ile Ile Ala Asp Tyr Tyr Arg
            50                  55                  60

Lys Phe Lys Gly Ser Gly Pro Phe Ala Gly Ile Phe Leu Gly His Lys
65                  70                  75                  80
```

```
Pro Ala Ala Val Val Leu Asp Lys Glu Leu Arg Lys Arg Val Leu Ile
            85                  90                  95
Lys Asp Phe Ser Asn Phe Ala Asn Arg Gly Leu Tyr Tyr Asn Glu Lys
            100                 105                 110
Asp Asp Pro Leu Thr Gly His Leu Val Met Val Glu Gly Glu Lys Trp
            115                 120                 125
Arg Ser Leu Arg Thr Lys Leu Ser Pro Thr Phe Thr Ala Gly Lys Met
    130                 135                 140
Lys Tyr Met Tyr Asn Thr Val Leu Glu Val Gly Gln Arg Leu Leu Glu
145                 150                 155                 160
Val Met Tyr Glu Lys Leu Glu Val Ser Ser Glu Leu Asp Met Arg Asp
                165                 170                 175
Ile Leu Ala Arg Phe Asn Thr Asp Val Ile Gly Ser Val Ala Phe Gly
            180                 185                 190
Ile Glu Cys Asn Ser Leu Arg Asn Pro His Asp Arg Phe Leu Ala Met
            195                 200                 205
Gly Arg Lys Ser Ile Glu Val Pro Arg His Asn Ala Leu Ile Met Ala
    210                 215                 220
Phe Ile Asp Ser Phe Pro Glu Leu Ser Arg Lys Leu Gly Met Arg Val
225                 230                 235                 240
Leu Pro Glu Asp Val His Gln Phe Phe Met Ser Ser Ile Lys Glu Thr
                245                 250                 255
Val Asp Tyr Arg Glu Lys Asn Asn Ile Arg Arg Asn Asp Phe Leu Asp
            260                 265                 270
Leu Val Leu Asp Leu Lys Asn Asn Pro Glu Ser Ile Ser Lys Leu Gly
            275                 280                 285
Gly Leu Thr Phe Asn Glu Leu Ala Ala Gln Val Phe Val Phe Phe Leu
    290                 295                 300
Gly Gly Phe Glu Thr Ser Ser Ser Thr Met Gly Phe Ala Leu Tyr Glu
305                 310                 315                 320
Leu Ala Gln Asn Gln Gln Leu Gln Asp Arg Leu Arg Glu Glu Val Asn
            325                 330                 335
Glu Val Phe Asp Gln Phe Lys Glu Asp Asn Ile Ser Tyr Asp Ala Leu
            340                 345                 350
Met Asn Ile Pro Tyr Leu Asp Gln Val Leu Asn Glu Thr Leu Arg Lys
    355                 360                 365
Tyr Pro Val Gly Ser Ala Leu Thr Arg Gln Thr Leu Asn Asp Tyr Val
    370                 375                 380
Val Pro His Asn Pro Lys Tyr Val Leu Pro Lys Gly Thr Leu Val Phe
385                 390                 395                 400
Ile Pro Val Leu Gly Ile His Tyr Asp Pro Glu Leu Tyr Pro Asn Pro
            405                 410                 415
Glu Glu Phe Asp Pro Glu Arg Phe Ser Pro Glu Met Val Lys Gln Arg
            420                 425                 430
Asp Ser Val Asp Trp Leu Gly Phe Gly Asp Gly Pro Arg Asn Cys Ile
    435                 440                 445
Gly Met Arg Phe Gly Lys Met Gln Ser Arg Leu Gly Leu Ala Leu Val
    450                 455                 460
Ile Arg His Phe Arg Phe Thr Val Cys Ser Arg Thr Asp Ile Pro Met
465                 470                 475                 480
Gln Ile Asn Pro Glu Ser Leu Ala Trp Thr Pro Lys Asn Asn Leu Tyr
                485                 490                 495
Leu Asn Val Gln Ala Ile Arg Lys Lys Ile Lys
            500                 505
```

( 2 ) INFORMATION FOR SEQ ID NO:23:

( i ) SEQUENCE CHARACTERISTICS:
        ( A ) LENGTH: 507 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: drosophila melanogaster
        ( B ) STRAIN:
        ( D ) DEVELOPMENTAL STAGE: Adult ( v i i i ) POSITION IN GENOME:
        ( A ) CHROMOSOME/SEGMENT:

( x i ) SEQUENCE DESCRIPTION: SEQ ID NO: 23:

```
Met Phe Val Leu Ile Tyr Leu Leu Ile Ala Ile Ser Ser Leu Leu Ala
 1               5                  10                  15

Tyr Leu Tyr His Arg Asn Phe Asn Tyr Trp Asn Arg Arg Gly Leu Pro
            20                  25                  30

His Asp Ala Pro His Pro Leu Tyr Gly Asn Met Val Gly Phe Arg Lys
        35                  40                  45

Asn Arg Val Met His Asp Phe Phe Tyr Asp Tyr Tyr Asn Lys Tyr Arg
    50                  55                  60

Lys Ser Gly Phe Pro Phe Val Gly Phe Tyr Phe Leu His Lys Pro Ala
65                  70                  75                  80

Ala Phe Ile Val Asp Thr Gln Leu Ala Lys Asn Ile Leu Ile Lys Asp
                85                  90                  95

Phe Ser Asn Phe Ala Asp Arg Gly Gln Phe His Asn Gly Arg Asp Asp
            100                 105                 110

Pro Leu Thr Gln His Leu Phe Asn Leu Asp Gly Lys Lys Trp Lys Asp
        115                 120                 125

Met Arg Gln Arg Leu Thr Pro Thr Phe Thr Ser Gly Lys Met Lys Phe
    130                 135                 140

Met Phe Pro Thr Val Ile Lys Val Ser Glu Glu Phe Val Lys Val Ile
145                 150                 155                 160

Thr Glu Gln Val Pro Ala Ala Gln Asn Gly Ala Val Leu Glu Ile Lys
                165                 170                 175

Glu Leu Met Ala Arg Phe Thr Thr Asp Val Ile Gly Thr Cys Arg Phe
            180                 185                 190

Gly Ile Glu Cys Asn Thr Leu Arg Thr Pro Val Ser Asp Phe Arg Thr
        195                 200                 205

Met Gly Gln Lys Val Phe Thr Asp Met Arg His Gly Lys Leu Leu Thr
    210                 215                 220

Met Phe Val Phe Ser Phe Pro Lys Leu Ala Ser Arg Leu Arg Met Arg
225                 230                 235                 240

Met Met Pro Glu Asp Val His Gln Phe Phe Met Arg Leu Val Asn Asp
                245                 250                 255

Thr Ile Ala Leu Arg Glu Arg Glu Asn Phe Lys Arg Asn Asp Phe Met
            260                 265                 270

Asn Leu Leu Ile Glu Leu Lys Gln Lys Gly Ser Ser Phe Thr Leu Asp
        275                 280                 285
```

|     |     |     |     |     |     |     |     |     |     |     |     |     |     |     |
| --- | --- | --- | --- | --- | --- | --- | --- | --- | --- | --- | --- | --- | --- | --- |
| Asn | Gly | Glu | Val | Ile | Glu | Gly | Met | Asp | Ile | Gly | Glu | Leu | Ala | Ala | Gln |
|     | 290 |     |     |     | 295 |     |     |     |     | 300 |     |     |     |     |     |
| Val | Phe | Val | Phe | Tyr | Val | Ala | Gly | Phe | Glu | Thr | Ser | Ser | Ser | Thr | Met |
| 305 |     |     |     |     | 310 |     |     |     |     | 315 |     |     |     |     | 320 |
| Ser | Tyr | Cys | Leu | Tyr | Glu | Leu | Ala | Gln | Asn | Gln | Asp | Ile | Gln | Asp | Arg |
|     |     |     |     | 325 |     |     |     |     | 330 |     |     |     |     | 335 |     |
| Leu | Arg | Asn | Glu | Ile | Gln | Thr | Val | Leu | Glu | Glu | Gln | Glu | Gly | Gln | Leu |
|     |     |     | 340 |     |     |     |     | 345 |     |     |     |     | 350 |     |     |
| Thr | Tyr | Glu | Ser | Ile | Lys | Ala | Met | Thr | Tyr | Leu | Asn | Gln | Val | Ile | Ser |
|     |     | 355 |     |     |     |     | 360 |     |     |     |     | 365 |     |     |     |
| Glu | Thr | Leu | Arg | Leu | Tyr | Thr | Leu | Val | Pro | His | Leu | Glu | Arg | Lys | Ala |
|     | 370 |     |     |     |     | 375 |     |     |     |     | 380 |     |     |     |     |
| Leu | Asn | Asp | Tyr | Val | Val | Pro | Gly | His | Glu | Lys | Leu | Val | Ile | Glu | Lys |
| 385 |     |     |     |     | 390 |     |     |     |     | 395 |     |     |     |     | 400 |
| Gly | Thr | Gln | Val | Ile | Ile | Pro | Ala | Cys | Ala | Tyr | His | Arg | Asp | Glu | Asp |
|     |     |     |     | 405 |     |     |     |     | 410 |     |     |     |     | 415 |     |
| Leu | Tyr | Pro | Asn | Pro | Glu | Thr | Phe | Asp | Pro | Glu | Arg | Phe | Ser | Pro | Glu |
|     |     |     | 420 |     |     |     |     | 425 |     |     |     |     | 430 |     |     |
| Lys | Val | Ala | Ala | Arg | Glu | Ser | Val | Glu | Trp | Leu | Pro | Phe | Gly | Asp | Gly |
|     |     |     | 435 |     |     |     |     | 440 |     |     |     |     | 445 |     |     |
| Pro | Arg | Asn | Cys | Ile | Gly | Met | Arg | Phe | Gly | Gln | Met | Gln | Ala | Arg | Ile |
|     | 450 |     |     |     |     | 455 |     |     |     |     | 460 |     |     |     |     |
| Gly | Leu | Ala | Gln | Ile | Ile | Ser | Arg | Phe | Arg | Val | Ser | Val | Cys | Asp | Thr |
| 465 |     |     |     |     | 470 |     |     |     |     | 475 |     |     |     |     | 480 |
| Thr | Glu | Ile | Pro | Leu | Lys | Tyr | Ser | Pro | Met | Ser | Ile | Val | Leu | Gly | Thr |
|     |     |     |     | 485 |     |     |     |     | 490 |     |     |     |     | 495 |     |
| Val | Gly | Gly | Ile | Tyr | Leu | Arg | Val | Glu | Arg | Ile |     |     |     |     |     |
|     |     |     | 500 |     |     |     |     | 505 |     |     |     |     |     |     |     |

( 2 ) INFORMATION FOR SEQ ID NO:24:

( i ) SEQUENCE CHARACTERISTICS:
        ( A ) LENGTH: 498 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: papillio polyxnes
        ( B ) STRAIN:
        ( D ) DEVELOPMENTAL STAGE: Adult ( v i i i ) POSITION IN GENOME:
        ( A ) CHROMOSOME/SEGMENT:

( x i ) SEQUENCE DESCRIPTION: SEQ ID NO: 24:

|     |     |     |     |     |     |     |     |     |     |     |     |     |     |     |
| --- | --- | --- | --- | --- | --- | --- | --- | --- | --- | --- | --- | --- | --- | --- |
| Met | Leu | Tyr | Leu | Leu | Ala | Leu | Val | Thr | Val | Leu | Ala | Gly | Leu | Leu | His |
| 1   |     |     |     | 5   |     |     |     |     | 10  |     |     |     |     | 15  |     |
| Tyr | Tyr | Phe | Thr | Arg | Thr | Phe | Asn | Tyr | Trp | Lys | Lys | Arg | Asn | Val | Ala |
|     |     |     | 20  |     |     |     |     | 25  |     |     |     |     | 30  |     |     |
| Gly | Pro | Lys | Pro | Val | Pro | Phe | Phe | Gly | Asn | Leu | Lys | Asp | Ser | Val | Leu |
|     |     | 35  |     |     |     |     | 40  |     |     |     |     | 45  |     |     |     |
| Arg | Arg | Lys | Pro | Gln | Val | Met | Val | Tyr | Lys | Ser | Ile | Tyr | Asp | Glu | Phe |
|     | 50  |     |     |     |     | 55  |     |     |     |     | 60  |     |     |     |     |
| Pro | Asn | Glu | Lys | Val | Leu | Gly | Ile | Tyr | Arg | Met | Thr | Thr | Pro | Ser | Val |

|  |  |  |  |  |  |  |  |  |  |  |  |  |  |  |  |
|---|---|---|---|---|---|---|---|---|---|---|---|---|---|---|---|
| 65 | | | | 70 | | | | 75 | | | | 80 | | | |
| Leu | Leu | Arg | Asp | Leu | Asp | Ile | Ile | Lys | His | Val | Leu | Ile | Lys | Asp | Phe |
| | | | | 85 | | | | 90 | | | | 95 | | | |
| Glu | Ser | Phe | Ala | Asp | Arg | Gly | Val | Glu | Phe | Ser | Leu | Asp | Gly | Leu | Gly |
| | | | 100 | | | | 105 | | | | | 110 | | | |
| Ala | Asn | Ile | Phe | His | Ala | Asp | Gly | Asp | Arg | Trp | Arg | Ser | Leu | Arg | Asn |
| | | | 115 | | | | 120 | | | | | 125 | | | |
| Arg | Phe | Thr | Pro | Leu | Phe | Thr | Ser | Gly | Lys | Leu | Lys | Ser | Met | Leu | Pro |
| | | 130 | | | | 135 | | | | | 140 | | | | |
| Leu | Met | Ser | Gln | Val | Gly | Asp | Arg | Phe | Ile | Asn | Ser | Ile | Asp | Glu | Val |
| 145 | | | | | 150 | | | | 155 | | | | | | 160 |
| Ser | Gln | Thr | Gln | Pro | Glu | Gln | Ser | Ile | His | Asn | Leu | Val | Gln | Lys | Phe |
| | | | | 165 | | | | 170 | | | | | 175 | | |
| Thr | Met | Thr | Asn | Ile | Ala | Ala | Cys | Val | Phe | Gly | Leu | Asn | Leu | Asp | Glu |
| | | | 180 | | | | | 185 | | | | 190 | | | |
| Gly | Met | Leu | Lys | Thr | Leu | Glu | Asp | Leu | Asp | Lys | His | Ile | Phe | Thr | Val |
| | | 195 | | | | 200 | | | | | 205 | | | | |
| Asn | Tyr | Ser | Ala | Glu | Leu | Asp | Met | Met | Tyr | Pro | Gly | Ile | Leu | Lys | Lys |
| | 210 | | | | | 215 | | | | | 220 | | | | |
| Leu | Asn | Gly | Ser | Leu | Phe | Pro | Lys | Val | Val | Ser | Lys | Phe | Phe | Asp | Asn |
| 225 | | | | | 230 | | | | | 235 | | | | | 240 |
| Leu | Thr | Lys | Asn | Val | Leu | Glu | Met | Arg | Lys | Gly | Thr | Pro | Ser | Tyr | Gln |
| | | | | 245 | | | | 250 | | | | | 255 | | |
| Lys | Asp | Met | Ile | Asp | Leu | Ile | Gln | Glu | Leu | Arg | Glu | Lys | Lys | Thr | Leu |
| | | | 260 | | | | 265 | | | | | 270 | | | |
| Glu | Leu | Ser | Arg | Lys | His | Glu | Asn | Glu | Asp | Val | Lys | Ala | Leu | Glu | Leu |
| | | 275 | | | | | 280 | | | | | 285 | | | |
| Thr | Asp | Gly | Val | Ile | Ser | Ala | Gln | Met | Phe | Ile | Phe | Tyr | Met | Ala | Gly |
| | 290 | | | | | 295 | | | | | 300 | | | | |
| Tyr | Glu | Thr | Ser | Ala | Thr | Thr | Met | Thr | Tyr | Leu | Phe | Tyr | Glu | Leu | Ala |
| 305 | | | | | 310 | | | | | 315 | | | | | 320 |
| Lys | Asn | Pro | Asp | Ile | Gln | Asp | Lys | Leu | Ile | Ala | Glu | Ile | Asp | Glu | Val |
| | | | | 325 | | | | 330 | | | | | 335 | | |
| Leu | Ser | Arg | His | Asp | Gly | Asn | Ile | Thr | Tyr | Glu | Cys | Leu | Ser | Glu | Met |
| | | | 340 | | | | | 345 | | | | | 350 | | |
| Thr | Tyr | Leu | Ser | Lys | Val | Phe | Asp | Glu | Thr | Leu | Arg | Lys | Tyr | Pro | Val |
| | | 355 | | | | | 360 | | | | | 365 | | | |
| Ala | Asp | Phe | Thr | Gln | Arg | Asn | Ala | Lys | Thr | Asp | Tyr | Val | Phe | Pro | Gly |
| | 370 | | | | | 375 | | | | | 380 | | | | |
| Thr | Asp | Ile | Thr | Ile | Lys | Lys | Gly | Gln | Thr | Ile | Ile | Val | Ser | Thr | Trp |
| 385 | | | | | 390 | | | | | 395 | | | | | 400 |
| Gly | Ile | Gln | Asn | Asp | Pro | Lys | Tyr | Tyr | Pro | Asn | Pro | Glu | Lys | Phe | Asp |
| | | | | 405 | | | | 410 | | | | | 415 | | |
| Pro | Glu | Arg | Phe | Asn | Pro | Glu | Asn | Val | Lys | Asp | Arg | His | Pro | Cys | Ala |
| | | | 420 | | | | | 425 | | | | | 430 | | |
| Tyr | Leu | Pro | Phe | Ser | Ala | Gly | Pro | Arg | Asn | Cys | Leu | Gly | Met | Arg | Phe |
| | | | 435 | | | | 440 | | | | | 445 | | | |
| Ala | Lys | Trp | Gln | Ser | Glu | Val | Cys | Ile | Met | Lys | Val | Leu | Ser | Lys | Tyr |
| | 450 | | | | | 455 | | | | | 460 | | | | |
| Arg | Val | Glu | Pro | Ser | Met | Lys | Ser | Ser | Gly | Pro | Phe | Lys | Phe | Asp | Pro |
| 465 | | | | | 470 | | | | | 475 | | | | | 480 |
| Met | Arg | Leu | Phe | Ala | Leu | Pro | Lys | Gly | Gly | Ile | Tyr | Val | Asn | Leu | Val |
| | | | | 485 | | | | 490 | | | | | 495 | | |

Arg Arg (2) INFORMATION FOR SEQ ID NO:25:

(i) SEQUENCE CHARACTERISTICS:
    (A) LENGTH: 504 amino acids
    (B) TYPE: amino acid
    (C) STRANDEDNESS: single
    (D) TOPOLOGY: linear (ii) MOLECULE TYPE: protein (iii) HYPOTHETICAL: NO (iv) ANTI-SENSE: NO (vi) ORIGINAL SOURCE:
    (A) ORGANISM: Rat
    (B) STRAIN:
    (D) DEVELOPMENTAL STAGE: Adult (viii) POSITION IN GENOME:
    (A) CHROMOSOME/SEGMENT:

(xi) SEQUENCE DESCRIPTION: SEQ ID NO: 25:

```
Met Asp Leu Leu Ser Ala Leu Thr Leu Glu Thr Trp Val Leu Leu Ala
  1               5                  10                  15

Val Val Leu Val Leu Leu Tyr Gly Phe Gly Thr Arg Thr His Gly Leu
             20                  25                  30

Phe Lys Lys Gln Gly Ile Pro Gly Pro Lys Pro Leu Pro Phe Phe Gly
         35                  40                  45

Thr Val Leu Asn Tyr Tyr Met Gly Leu Trp Lys Phe Asp Val Glu Cys
     50                  55                  60

His Lys Lys Tyr Gly Lys Ile Trp Gly Leu Phe Asp Gly Gln Met Pro
 65                  70                  75                  80

Leu Phe Ala Ile Thr Asp Thr Glu Met Ile Lys Asn Val Leu Val Lys
                 85                  90                  95

Glu Cys Phe Ser Val Phe Thr Asn Arg Arg Asp Phe Gly Pro Val Gly
                100                 105                 110

Ile Met Gly Lys Ala Val Ser Val Ala Lys Asp Glu Glu Trp Lys Arg
            115                 120                 125

Tyr Arg Ala Leu Leu Ser Pro Thr Phe Thr Ser Gly Arg Leu Lys Glu
        130                 135                 140

Met Phe Pro Ile Ile Glu Gln Tyr Gly Asp Ile Leu Val Lys Tyr Leu
145                 150                 155                 160

Lys Gln Glu Ala Glu Thr Gly Lys Pro Val Thr Met Lys Lys Val Phe
                165                 170                 175

Gly Ala Tyr Ser Met Asp Val Ile Thr Ser Thr Ser Phe Gly Val Asn
            180                 185                 190

Val Asp Ser Leu Asn Asn Pro Lys Asp Pro Phe Val Glu Lys Thr Lys
        195                 200                 205

Lys Leu Leu Arg Phe Asp Phe Phe Asp Pro Leu Phe Leu Ser Val Val
    210                 215                 220

Leu Phe Pro Phe Leu Thr Pro Ile Tyr Glu Met Leu Asn Ile Cys Met
225                 230                 235                 240

Phe Pro Lys Asp Ser Ile Glu Phe Phe Lys Lys Phe Val Tyr Arg Met
                245                 250                 255

Lys Glu Thr Arg Leu Asp Ser Val Gln Lys His Arg Val Asp Phe Leu
            260                 265                 270

Gln Leu Met Met Asn Ala His Asn Asp Ser Lys Asp Lys Glu Ser His
        275                 280                 285
```

```
Thr  Ala  Leu  Ser  Asp  Met  Glu  Ile  Thr  Ala  Gln  Ser  Ile  Ile  Phe  Ile
     290                 295                      300

Phe  Ala  Gly  Tyr  Glu  Pro  Thr  Ser  Ser  Thr  Leu  Ser  Phe  Val  Leu  His
305                      310                      315                      320

Ser  Leu  Ala  Thr  His  Pro  Asp  Thr  Gln  Lys  Lys  Leu  Gln  Glu  Glu  Ile
               325                      330                           335

Asp  Arg  Ala  Leu  Pro  Asn  Lys  Ala  Pro  Pro  Thr  Tyr  Asp  Thr  Val  Met
               340                 345                      350

Glu  Met  Glu  Tyr  Leu  Asp  Met  Val  Leu  Asn  Glu  Thr  Leu  Arg  Leu  Tyr
          355                      360                      365

Pro  Ile  Gly  Asn  Arg  Leu  Glu  Arg  Val  Cys  Lys  Lys  Asp  Val  Glu  Ile
     370                      375                      380

Asn  Gly  Val  Phe  Met  Pro  Lys  Gly  Ser  Val  Val  Met  Ile  Pro  Ser  Tyr
385                      390                      395                      400

Ala  Leu  His  Arg  Asp  Pro  Gln  His  Trp  Pro  Glu  Pro  Glu  Glu  Phe  Arg
               405                      410                           415

Pro  Glu  Arg  Phe  Ser  Lys  Glu  Asn  Lys  Gly  Ser  Ile  Asp  Pro  Tyr  Val
               420                 425                      430

Tyr  Leu  Pro  Phe  Gly  Asn  Gly  Pro  Arg  Asn  Cys  Ile  Gly  Met  Arg  Phe
          435                 440                      445

Ala  Leu  Met  Asn  Met  Lys  Leu  Ala  Leu  Thr  Lys  Val  Leu  Gln  Asn  Phe
450                      455                      460

Ser  Phe  Gln  Pro  Cys  Lys  Glu  Thr  Gln  Ile  Pro  Leu  Lys  Leu  Ser  Arg
465                      470                      475                      480

Gln  Gly  Leu  Leu  Gln  Pro  Thr  Lys  Pro  Ile  Ile  Leu  Lys  Val  Val  Pro
                    485                      490                      495

Arg  Asp  Glu  Ile  Ile  Thr  Gly  Ser
               500
```

(2) INFORMATION FOR SEQ ID NO:26:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Musca domestica
        (B) STRAIN: Learn-PyR
        (D) DEVELOPMENTAL STAGE: Adult (viii) POSITION IN GENOME:
        (A) CHROMOSOME/SEGMENT: Chromosome 1

(xi) SEQUENCE DESCRIPTION: SEQ ID NO: 26:

```
Phe  Xaa  Xaa  Pro  Xaa  Xaa  Tyr  Xaa  Pro  Xaa  Arg  Phe
1                   5                        10
```

(2) INFORMATION FOR SEQ ID NO:27:

(i) SEQUENCE CHARACTERISTICS:
        (A) LENGTH: 1551 base pairs
        (B) TYPE: nucleic acid
        (C) STRANDEDNESS: single
        (D) TOPOLOGY: linear ( i i ) MOLECULE TYPE: DNA (cDNA)

( i i i ) HYPOTHETICAL: NO ( i v ) ANTI-SENSE: NO ( v i ) ORIGINAL SOURCE:
    ( A ) ORGANISM: Musca domestica
    ( B ) STRAIN: CS
    ( D ) DEVELOPMENTAL STAGE: Adult ( v i i i ) POSITION IN GENOME:
    ( A ) CHROMOSOME/SEGMENT: Chromosome 1

( x i ) SEQUENCE DESCRIPTION: SEQ ID NO: 27:

```
ATGTTGTTAT TACTGCTACT GATTGTGGTG ACGACCCTCT ACATCTTTGC CAAACTTCAT   60
TATACGAAAT GGGAACGTTT GGGTTTCGAA TCGGATAAGG CCACCATACC CCTGGGATCG  120
ATGGCAAAGG TGTTCCACAA GGAACGGCCA TTTGGCCTGG TTATGTCCGA CATATATGAC  180
AAATGCCACG AGAAGGTGGT GGGCATTTAT TTGTTCTTCA AGCCGGCCCT ACTGGTGCGC  240
GATGCCGAAT TGGCGAGACA AATTTTGACC ACGGATTTTA ATAGCTTCCA TGATCGTGGC  300
CTCTATGTGG ATGAGAAAAA TGATCCAATG TCGGCGAATC TTTTCGTGAT GGAGGGTCAA  360
TCATGGCGTA CGCTGAGAAT GAAATTGGCC CCCTCGTTTT CGTCGGGTAA ACTCAAGGGG  420
ATGTTCGAAA CGGTCGATGA TGTGGCGGAT AAATTAATAA ATCACTTGAA TGAGCGCTTG  480
AAGGATGGCC AGACGCATGT TTTGGAAATC AAGAGTATTT TGACCACCTA TGCTGTCGAC  540
ATCATTGGTT CGGTGATATT CGGCCTGGAA ATCGATAGTT TCACCCATCC GGACAATGAA  600
TTTCGTGTCT TGAGTGATCG TCTATTTAAC CCAAAGAAGT CGACAATGTT GGAGAGATTT  660
CGCAATTTAT CAACCTTTAT GTGTCCACCA CTTGCCAAAC TCTTGTCGCG CCTTGGTGCC  720
AAGGATCCGA TAACATATCG CCTGCGCGAC ATCGTGAAAC GGACGATAGA ATTTCGCGAA  780
GAAAAGGGCG TTGTACGCAA AGATCTTCTC CAGCTATTTA TACAACTCAG AAATACTGGT  840
AAAATTTCCG ATGACAACGA CAAGCTATGG CATGACGTTG AGTCGACGGC GGAAAATCTC  900
AAAGCCATGT CCATCGATAT GATTGCCTCC AATTCATTCT TATTCTATAT TGCCGGATCG  960
GAAACAACGG CGGCCACAAC ATCATTTACC ATCTATGAAT TGGCCATGTA TCCGGAAATT 1020
CTGAAGAAGG CCCAAAGCGA GGTGGATGAG TGTCTGCAAA GGCACGGTCT CAAGCCGCAG 1080
GGACGGCTGA CCTATGAGGC CATACAGGAT ATGAAATATT TGGATTTGTG TGTTATGGAA 1140
ACCACCCGCA AATACCCTGG CCTGCCGTTT TTGAATCGCA AATGCACTCA GGATTTCCAA 1200
GTACCCGACA CAAAACTTAC CATACCCAAG GAAACGGGAA TTATCATCTC CCTCTTGGGC 1260
ATCCATAGAG ACCCACAGTA TTTCCCCCAA CCCGAGGATT ATAGGCCAGA ACGCTTTGCC 1320
GATGAGAGCA AGGATTATGA TCCAGCGGCA TATATGCCTT TTGGAGAGGG TCCAAGGCAC 1380
TGTATTGCTC AACGCATGGG CGTTATGAAT TCCAAGGTAG CCTTGGCCAA AATATTGGCC 1440
AATTTTAATA TTCAACCAAT GCCCCGCCAA GAAGTTGAGT CAAATTCCA TTCAGCTCCT 1500
GTTCTGGTAC CAGTAAATGG TCTCAATGTG GGTCTATCGA AGAGGTGGTG A          1551
```

( 2 ) INFORMATION FOR SEQ ID NO:28:

( i ) SEQUENCE CHARACTERISTICS:
        ( A ) LENGTH: 517 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
    ( A ) ORGANISM: Musca domestica
    ( B ) STRAIN: CS
    ( D ) DEVELOPMENTAL STAGE: Adult ( v i i i ) POSITION IN GENOME:
    ( A ) CHROMOSOME/SEGMENT: Chromosome 1

( x i ) SEQUENCE DESCRIPTION: SEQ ID NO: 28:

| | | | | | | | | | | | | | | |
|---|---|---|---|---|---|---|---|---|---|---|---|---|---|---|
| Met | Leu | Leu | Leu | Leu | Leu | Leu | Ile | Val | Val | Thr | Thr | Leu | Tyr | Ile | Phe |
| 1 | | | | 5 | | | | | 10 | | | | | 15 | |
| Ala | Lys | Leu | His | Tyr | Thr | Lys | Trp | Glu | Arg | Leu | Gly | Phe | Glu | Ser | Asp |
| | | | 20 | | | | | 25 | | | | 30 | | | |
| Lys | Ala | Thr | Ile | Pro | Leu | Gly | Ser | Met | Ala | Lys | Val | Phe | His | Lys | Glu |
| | | | 35 | | | | 40 | | | | | 45 | | | |
| Arg | Pro | Phe | Gly | Leu | Val | Met | Ser | Asp | Ile | Tyr | Asp | Lys | Cys | His | Glu |
| | 50 | | | | | 55 | | | | | 60 | | | | |
| Lys | Val | Val | Gly | Ile | Tyr | Leu | Phe | Phe | Lys | Pro | Ala | Leu | Leu | Val | Arg |
| 65 | | | | | 70 | | | | | 75 | | | | | 80 |
| Asp | Ala | Glu | Leu | Ala | Arg | Gln | Ile | Leu | Thr | Thr | Asp | Phe | Asn | Ser | Phe |
| | | | | 85 | | | | | 90 | | | | | 95 | |
| His | Asp | Arg | Gly | Leu | Tyr | Val | Asp | Glu | Lys | Asn | Asp | Pro | Met | Ser | Ala |
| | | | 100 | | | | | 105 | | | | 110 | | | |
| Asn | Leu | Phe | Val | Met | Glu | Gly | Gln | Ser | Trp | Arg | Thr | Leu | Arg | Met | Lys |
| | | 115 | | | | | 120 | | | | | 125 | | | |
| Leu | Ala | Pro | Ser | Phe | Ser | Ser | Gly | Lys | Leu | Lys | Gly | Met | Phe | Glu | Thr |
| | 130 | | | | | 135 | | | | | 140 | | | | |
| Val | Asp | Asp | Val | Ala | Asp | Lys | Leu | Ile | Asn | His | Leu | Asn | Glu | Arg | Leu |
| 145 | | | | | 150 | | | | | 155 | | | | | 160 |
| Lys | Asp | Gly | Gln | Thr | His | Val | Leu | Glu | Ile | Lys | Ser | Ile | Leu | Thr | Thr |
| | | | | 165 | | | | | 170 | | | | | 175 | |
| Tyr | Ala | Val | Asp | Ile | Ile | Gly | Ser | Val | Ile | Phe | Gly | Leu | Glu | Ile | Asp |
| | | | 180 | | | | | 185 | | | | | 190 | | |
| Ser | Phe | Thr | His | Pro | Asp | Asn | Glu | Phe | Arg | Val | Leu | Ser | Asp | Arg | Leu |
| | | 195 | | | | | 200 | | | | | 205 | | | |
| Phe | Asn | Pro | Lys | Lys | Ser | Thr | Met | Leu | Glu | Arg | Phe | Arg | Asn | Leu | Ser |
| | 210 | | | | | 215 | | | | | 220 | | | | |
| Thr | Phe | Met | Cys | Pro | Pro | Leu | Ala | Lys | Leu | Leu | Ser | Arg | Leu | Gly | Ala |
| 225 | | | | | 230 | | | | | 235 | | | | | 240 |
| Lys | Asp | Pro | Ile | Thr | Tyr | Arg | Leu | Arg | Asp | Ile | Val | Lys | Arg | Thr | Ile |
| | | | | 245 | | | | | 250 | | | | | 255 | |
| Glu | Phe | Arg | Glu | Glu | Lys | Gly | Val | Val | Arg | Lys | Asp | Leu | Leu | Gln | Leu |
| | | | 260 | | | | | 265 | | | | | 270 | | |
| Phe | Ile | Gln | Leu | Arg | Asn | Thr | Gly | Lys | Ile | Ser | Asp | Asp | Asn | Asp | Lys |
| | | 275 | | | | | 280 | | | | | 285 | | | |
| Leu | Trp | His | Asp | Val | Glu | Ser | Thr | Ala | Glu | Asn | Leu | Lys | Ala | Met | Ser |
| | 290 | | | | | 295 | | | | | 300 | | | | |
| Ile | Asp | Met | Ile | Ala | Ser | Asn | Ser | Phe | Leu | Phe | Tyr | Ile | Ala | Gly | Ser |
| 305 | | | | | 310 | | | | | 315 | | | | | 320 |
| Glu | Thr | Thr | Ala | Ala | Thr | Thr | Ser | Phe | Thr | Ile | Tyr | Glu | Leu | Ala | Met |
| | | | | 325 | | | | | 330 | | | | | 335 | |
| Tyr | Pro | Glu | Ile | Leu | Lys | Lys | Ala | Gln | Ser | Glu | Val | Asp | Glu | Cys | Leu |
| | | | 340 | | | | | 345 | | | | 350 | | | |
| Gln | Arg | His | Gly | Leu | Lys | Pro | Gln | Gly | Arg | Leu | Thr | Tyr | Glu | Ala | Ile |

|     |     |     |     |     |     |     |     |     |     |     |     |     |     |
| --- | --- | --- | --- | --- | --- | --- | --- | --- | --- | --- | --- | --- | --- |
|     |     |     |     | 355 |     |     |     |     | 360 |     |     |     | 365 |

Gln Asp Met Lys Tyr Leu Asp Leu Cys Val Met Glu Thr Thr Arg Lys
370                     375                 380

Tyr Pro Gly Leu Pro Phe Leu Asn Arg Lys Cys Thr Gln Asp Phe Gln
385                     390                 395                 400

Val Pro Asp Thr Lys Leu Thr Ile Pro Lys Glu Thr Gly Ile Ile Ile
                405                 410                         415

Ser Leu Leu Gly Ile His Thr His Pro Gln Tyr Phe Pro Gln Pro Glu
            420                 425                 430

Asp Tyr Arg Pro Glu Arg Phe Ala Asp Glu Ser Lys Asp Tyr Asp Pro
        435                 440                 445

Ala Ala Tyr Met Pro Phe Gly Glu Gly Pro Arg His Cys Ile Ala Gln
450                     455                 460

Arg Met Gly Val Met Asn Ser Lys Val Ala Leu Ala Lys Ile Leu Ala
465                     470                 475                 480

Asn Phe Asn Ile Gln Pro Met Pro Arg Gln Glu Val Glu Phe Lys Phe
                485                 490                 495

His Ser Ala Pro Val Leu Val Pro Val Asn Gly Leu Asn Val Gly Leu
            500                 505                 510

Ser Lys Arg Trp Xaa
515

( 2 ) INFORMATION FOR SEQ ID NO:29:

( i ) SEQUENCE CHARACTERISTICS:
( A ) LENGTH: 2085 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Musca domestica
( B ) STRAIN: Learn-PyR
( D ) DEVELOPMENTAL STAGE: Adult ( v i i i ) POSITION IN GENOME:
( A ) CHROMOSOME/SEGMENT: Chromosome 1

( x i ) SEQUENCE DESCRIPTION: SEQ ID NO: 29:

```
GACAGGGAGA  AGGAAATGAT  AAGAAATGTG  CAAAGTTTTA  CATGCATTCG  AATCATTCTG      60
TTTCACAAAA  TGACCGGCAA  CTATTCAGTT  GTTAATGTAA  CACGTACCCG  ATTAGATCGG     120
AAATATTTTG  TAACGTTAGT  GAATAGCTAG  GAGAAAAATT  GCAAAACTAA  AATGTTGTTA     180
TTACTGCTAC  TGATTGTGGT  GACGACCCTC  TACATCTTTG  CCAAACTTCA  TTATACGAAA     240
TGGGAACGTT  TGGGTTTCGA  ATCGGATAAG  GCCACCATAC  CCTGGGATC   GATGGCAAAG     300
GTGTTCCACA  AGGAACGGCC  ATTTGGCCTG  GTTATGTCAG  ACATATACGA  CAAATGCCAC     360
GAGAAGGTGG  TGGGCATTTA  TTTGTTCTTC  AAGCCGGCCC  TACTGGTGCG  CGATGCCGAA     420
TTGGCGAGAC  AAATTTTGAC  CACGGATTTT  AATAGCTTCC  ATGATCGTGG  CCTCTATGTG     480
GATGAGAAAA  ATGATCCAAT  GTCGGCGAAT  CTTTTCGTGA  TGGAGGGTCA  ATCATGGCGT     540
ACGCTGAGAA  TGAAATTGGC  CCCCTCGTTT  TCGTCGGGTA  AACTCAAGGG  GATGTTCGAA     600
ACGGTCGATG  ATGTGGCGGA  TAAATTAATA  AATCACTTGA  ATGAGTGCTT  GAAGGATGGC     660
CAGACGCATG  TTTTGGAAAT  CAAGAGTATT  TTGACCACGT  AAGTACTCAT  CGTTGAGAGA     720
```

```
ATTGTAAGAA GTTTTGAATT TTACTTTTAA TAAAATGTTC TTCTTCCCCC AGCTATGCTG    780
TCGACATCAT TGGTTCGGTG ATATTCGGCC TGGAAATCGA TAGTTTCACC CATCCGGACA    840
ATGAATTTCG TGTCTTGAGT GATCGTCTAT TTAACCCAAA GAAGTCGACA ATGTTGGAGA    900
GATTTCGCAA TTTATCAACC TTTATGTGTC TACCACTTGC CAAACTCTTG TCGCGCCTTG    960
GTGCCAAGGA TCCGATAACA TATCGCCTGC GCGACATCGT GAAACGGACG ATAGAATTTC   1020
GCGAAGAAAA GGGCGTTGTA CGCAAAGATC TTCTCCAGCT ATTTATACAA CTCAGAAATA   1080
CTGGTAAAAT TTCCGATGAC AACGACAAGC TATGGCATGA CGTTGAGTCG ACGGCGGAAA   1140
ATCTCAAAGC CATGTCCATC GATATGATTG CCTCCAATTC ATTCTTATTC TATATTGCCG   1200
GATCGGAAAC AACGGCGGCC ACAACATCAT CTACCATCTA TGAATTGGCC ATGTATCCGG   1260
AAATTCTGAA GAAGGCCCAA AGCGAGGTGG ATGAGTGTCT GCAAAGGCAC GGTCCCAAGC   1320
CGCAGGGACG GCTGACCTAT GAGGCCATAC AGGATATGAA ATATTTGGAT TTGTGTGTTA   1380
TGGGTAAGAG GGGAAATTTT GAAATTGTTT TTTTTTTTA TTTTCTAATT ATTGCATGTT   1440
TTTGTTGTAG AAACCACCCG CAAATACCCT GGCCTGCCGT TTTGAATCG CAAATGCACT   1500
CAGGATTTCC AAGTACCCGA CACAAAACTT ACCATACCCA AGGAAACGGG AATTATCATC   1560
TCCCTCTTGG GCATCCATAG AGACCCACAG TATTTCTCCC AACCCGAGGA TTATAGGCCA   1620
GAACGCTTTG CCGATGAGAG CAAGGATTAT GATCCAGCGG CATATATGCC TTTTGGAGAG   1680
GGTCCAAGGC ACTGTATTGG TGAGATGTTG AAAGGGGAGC TTCATTAAAT TCTGAATATT   1740
AATTTGTAT TTTTTTCCA CACCGCTCAA CGCATGGGCG TTATGAATTC CAAGGTAGCC   1800
TTGGCCAAAA TATTGGCCAA TTTTAATATT CAACCAATGC CCGCCAAGA AGTTGAGTTC   1860
AAATTCCATT CAGCTCCTGT TCTGGTACCA GTAAATGGTC TCAATGTGGG TCTATCGAAG   1920
AGGTGGTGAA GAGCAAGTGG TTAAGTGAAT TGAGGAGTGC TTTTTCGAGA TATATGTTGG   1980
TGATTAGGGT TATAACGATT ATTTAAGAAC CAGTATTTAA GCTTTAATTT TTTATTCAAA   2040
ATTTTTGAAA TATTGAAATT AAAATAAACA TATGTAAATA AAATT                   2085
```

CYTOCHROME P450$_{LPR}$ GENE AND ITS USES

This is a division of application Ser. No. 08/241,388 filed on May 10, 1994.

The subject matter of this application was made with support from the United States Government (National Institutes of Health Grant No. R01 GM47835-01 and United States Department of Agriculture Grant No. 9001168).

FIELD OF THE INVENTION

The present invention relates to the cytochrome P450$_{lpr}$ gene and its uses.

BACKGROUND OF THE INVENTION

The microsomal cytochrome P450-dependent monooxygenases (hereafter called "P450 monooxygenases") are an extremely important metabolic system involved in the detoxication of xenobiotics such as drugs, pesticides, and plant toxins; and in the regulation of endogenous compounds such as hormones, fatty acids, and steroids. P450 monooxygenases are found in almost all aerobic organisms, including organisms as diverse as plants, insects, mammals, birds, and fungi. See U.S. Pat. Nos. 4,766,068 to Oeda, et al., 5,164,313 to Gelboin, et al., and 5,212,296 to Dean, et al. In eucaryotes, P450 monooxygenases are typically found in the endoplasmic reticulum of metabolically active tissues. The two most important components of the P450 monooxygenases are cytochrome P450, which acts as the substrate binding protein (and terminal oxidase), and NADPH-cytochrome P450 reductase (P450 reductase), which transfers electrons from NADPH to cytochrome P450. Cytochrome b5 may have a role in P450 monooxygenase activity by donating an (i.e., the second) electron to P450 (via cytochrome b5 reductase) or by modulating P450 monooxygenase activity through inhibitory or stimulatory interactions with P450. See S. Kawano, et al., *J. Biochem.*, 102:493 (1987) and I. Golly, et al., *Arch. Biochem. Biophys.*, 260:232 (1988), which are hereby incorporated by reference. However, the exact importance of cytochrome b5 is still questioned, because it is not required for activity in most reconstituted P450 monooxygenase systems. The role of cytochrome b5 and Cytochrome b5 reductase in P450 monooxygenase activity in insects is poorly understood.

P450 monooxygenases are capable of oxidizing a bewildering array of xenobiotics, E. Hodgson, "Microsomal mono-oxygenases," *Comprehensive Insect Physiology Biochemistry and Pharmacology*, Vol. 11, G. A. Kerkut and L. I. Gilbert, eds., Pergamon Press, Oxford (1985), which is hereby incorporated by reference. This remarkable breadth of utilizable substrates is due to the large number of cytochrome P450 forms that are expressed in each organism. For instance, over 13 P450s have been isolated from rats, F. P. Guengerich, "Enzymology of Rat Liver Cytochrome P450, in: "Mammalian Cytochrome P450", Vol. 1, F. P. Guengerich, ed., CRC Press, Boca Raton, Fla. (1987), which is hereby incorporated by reference, and 221 cytochrome P450 cDNA sequences have been described mostly from mammalian systems, D. R. Nelson, et al., "The P450 Superfamily: Update on New Sequences, Gene Mapping, Accession Numbers, Early Trivial Names of Enzymes, and Nomenclature," *DNA Cell Biol.*, 12:1–51 (1993), which is hereby incorporated by reference. The specificity of the P450 monooxygenase system, therefore, is dependent on the P450 cytochrome(s) present, many with apparently overlapping specificity. This complexity requires that individual cytochrome P450 forms be isolated in order to understand and characterize their contribution to important metabolic functions.

The P450 monooxygenases in insects are extremely important for growth, development, feeding, resistance to pesticides, and tolerance to plant toxins, M. Agosin, "Role of Microsomal Oxidation in Insecticide Degradation", *Comprehensive Insect Physiology, Biochemistry and Pharmacology*, Vol. 12, G. A. Kerkut and L. I. Gilbert, eds., Pergamon Press, Oxford (1985) and E. Hodgson, "The Significance of Cytochrome P450 in Insects," Insect Biochem., 13:237–246 (1983), which are hereby incorporated by reference. Furthermore, P450 monooxygenases are intimately involved in the synthesis and degradation of insect hormones and pheromones including 20-hydorxyecdysone and juvenile hormone, M. Agosin, "Role of Microsomal Oxidation in Insecticide Degradation," *Comprehensive Insect Physiology, Biochemistry and Pharmacology*, Vol. 12, G. A. Kerkut and L. I. Gilbert, eds., Pergamon Press, Oxford (1985), which is hereby incorporated by reference. Insect P450 monooxygenases can be detected in a wide range of tissues. Highest P450 monooxygenase activities are usually associated with the midgut, fat body, and Malpighian tubules, Id. and E. Hodgson, "The Significance of Cytochrome P450 in insects, *Insect Biochem.*, 13:237–246 (1983), which are hereby incorporated by reference. Dramatic variations in the levels of cytochrome P450 and monooxygenase activity are seen during the development of most insects, Id. and D. R. Vincent, et al., "Cytochrome P450 in Insects. 6. Age Dependency and Phenobarbital Inducibility of Cytochrome P-450 Reductase and Monooxygenase Activity in Susceptible and Resistant Strains of *Musca domestica*," *Pestic. Biochem. Physiol.*, 23:171–81 (1985), which are hereby incorporated by reference. In general, P450 levels are undetectable in eggs, rise and fall in each larval instar, are undetectable in pupae, and are expressed at high levels in adults. M. Agosin, "Role of Microsomal Oxidation in Insecticide Degradation," *Comprehensive Insect Physiology, Biochemistry and Pharmacology*, Vol. 12, G. A. Kerkut and L. I. Gilbert, eds., Pergamon Press, Oxford (1985), which is hereby incorporated by reference.

The role of monooxygenases in insecticide resistance first became apparent in the early 1960s, when Eldefrawi, et al., "Methylenedioxyphenyl Derivatives as Synergists for Carbamate Insecticides in Susceptible, DDT-, and Parathion-Resistant House Flies," *J. Econ. Entomol.*, 53:231–34 (1960), which is hereby incorporated by reference, showed that resistance to carbaryl could be abolished by the methylenedioxyphenyl cytochrome P450 inhibitor sesamex. Additional evidence of monooxygenase-based resistance quickly accumulated. G. P. Georghiou, et al., "The Absorption and Metabolism of 3-isopropyl-phenyl N-methylcarbamate by Susceptible and Carbamate-Selected Strains of House Flies," *J. Econ. Entomol.*, 54:231–33 (1961), G. P. Georghiou, et al., "The Development and Characterization of Resistance to Carbamate Insecticides in the House Fly, *Musca domestica*," *J. Econ. Entomol.*, 54:132–140 (1961), and R. D. Schonbrod, et al., "Hydroxylation as a Factor in Resistance in House Flies and Blow Flies," *J. Econ. Entomol.*, 58:74–78 (1965), which are hereby incorporated by reference. In 1967, Tsukamoto and Casida (M. Tsukamoto, et al., "Metabolism of Methylcarbamate Insecticides by the NADPH$_2$-requiring Enzyme System from Houseflies," *Nature London*, 213:49–51 (1967), which is hereby incorporated by reference) showed that carbamate-resistant house flies exhibited increased ability, compared to susceptible flies, to perform oxidative hydroxylations, N-demethylations, O-demethylations, epoxidations, and desulfurations. Soon after, other workers showed the diazinon-resistant Fc strain had increased ability to oxidize DDT, F. J. Oppenoorth, et al., "DDT Resistance in the Housefly Caused by Microsomal Degradation", *Ent. Exp. Appl.*, 11:81–93 (1968), which is hereby incorporated by reference, and aldrin and naphthalene, R. D. Schonbrod, et al., "Microsomal Oxidases in the House Fly: A Survey of Fourteen Strains," *Life Sci.* 7:681–688 (1968), which is hereby incorporated by reference. Increased ability to metabolize many substrates was shown in other insecticide-resistant house fly strains such as Rutgers diazinon-resistant strain, M. D. Folsom, et al., "Biochemical Characteristics of Microsomal Preparations from Diazinon-resistant and -susceptible Houseflies," *Life Sci.* 9:869–875 (1970), which is hereby incorporated by reference. In addition, increased levels of total cytochrome P450 were found in several insecticide-resistant strains such as Diazinon-R, Fc, R-Baygon, Dimethoate-R, Orlando-R, Malathion-R, and Ronnel-R. E. Hodgson, "Microsomal Mono-oxygenases," *Comprehensive Insect Physiology Biochemistry and Pharmacology*, G. A. Kerkut, et al., eds., Pergamon Press, Oxford, 11:225–321 (1985), which is hereby incorporated by reference.

We now know that insects commonly become resistant to insecticides due to increased detoxication mediated by the cytochrome P450 monooxygenase system. This resistance mechanism is very important, because it can confer both high levels of resistance, L. B. Brattsten, et al., "Insecticide Resistance: Challenge to Pest Management and Basic Research," *Science*, 231:1255–60 (1986) and J. G. Scott, et al., "Mechanisms Responsible for High Levels of Permethrin Resistance in the House Fly," *Pestic. Sci.*, 17:195–206 (1986), which are hereby incorporated by reference, and may also confer cross-resistance to unrelated compounds due to the breadth of substrates the P450 monooxygenases can metabolize. J. G. Scott, "Insecticide Resistance in Insects," *Handbook of Pest Management*, Vol. 2, D. Pimentel, ed., CRC Press, Boca Raton, Fla. (1991), which is hereby incorporated by reference. Furthermore, P450 monooxygenase-mediated detoxication has been found as a mechanism of resistance in a large number of important pests. C. F. Wilkinson, "Role of Mixed-function Oxidases in Insecticide Resistance," *Pest Resistance in Pesticides*, G. P. Georghiou and T. Saito, eds., Plenum Press, New York (1983), which is hereby incorporated by reference.

Purification of a P450 from insects in useful quantity and quality remained elusive for many years due to the difficulties encountered in insect cytochrome P450 purification. E. Hodgson, "Microsomal mono-oxygenases," *Comprehensive Insect Physiology Biochemistry and Pharmacology*, Vol. 11, G. A. Kerkut and L. I. Gilbert, eds., Pergamon Press, Oxford (1985) and C. W. Fisher, et al., "Partial Purification and Characterization of Phenobarbital-Induced House Fly P-450," *Arch. Insect Biochem. Physiol.*, 1:127–38 (1984), which are hereby incorporated by reference. R. D. Schonbrod, et al., "The Solubilization and Separation of Two Forms of Microsomal cytochrome P-450 from the House Fly, *Musca domestica*," *Biochem. Biophys. Res. Comm.*, 64:829–833 (1975), which is hereby incorporated by reference, reported resolution of two forms of low specific content (impure or damaged cytochrome P450 preparations) but produced early evidence of multiplicity of cytochrome P450 in house flies. An early attempt, J. Capdevila, et al., "Multiple Forms of Housefly Cytochrome P-450," *Microsomes and Drug Oxidations*, V. Ulrich, ed., Pergamon Press, New York (1977), which is hereby incorporated by reference, using uninduced, susceptible house flies was remarkably successful, isolating one P450 with high specific content (13.9 nmol cytochrome P450/mg protein) but impure based on gel electrophoresis. This method required seven open-column chromatographic steps and apparently was not pursued further. The resolution of several impure cytochrome P450 preparations was reported by S. J. Yu, et al., "Cytochrome P-450 in insects. 1. Differences in the Forms Present in Insecticide Resistant and Susceptible House Flies," *Pestic. Biochem. Physiol.*, 12:239–48 (1979), which is hereby incorporated by reference. A. F. Moldenke, et al., "Cytochrome P-450 in Insects 4. Reconstitution of Cytochrome P-450-dependent monooxygenase Activity in the House Fly," *Pestic. Biochem. Physiol.*, 21:358–67 (1984), which is hereby incorporated by reference, resolved two crude cytochrome P450 fractions and reconstituted the Oxidase activity with purified cytochrome P450 reductase to show that different cytochrome P450 fractions have different metabolic capabilities. In the same year, C. W. Fisher, et al., "Partial Purification and Characterization of Phenobarbital-. Induced House Fly P-450," *Arch. Insect Biochem. Physiol.*, 1:127–38 (1984), which is hereby incorporated by reference, reported a partially pure preparation from the Rutgers diazinon-resistant strain with a specific content of 10 nmol/mg and partially characterized it. M. J. J. Ronis, et al., "Characterization of Multiple Forms of Cytochrome P-450 From an Insecticide Resistant Strain of House Fly (*Musca domestica*)," *Pestic. Biochem. Physiol.*, 32:74–90 (1988), which is hereby incorporated by reference, partially purified several P450s from the Rutgers strain with specific contents ranging between 2.5 and 7 nmol/mg and showed that they could, with limited success, be reconstituted with mammalian cytochrome P450 reductase. However, a biochemically useful purification of a cytochrome P450 from an insect, and more importantly from an insecticide-resistant house fly, remained elusive for many years.

In 1989, the purification of a major cytochrome P450, termed P450$_{lpr}$, from LPR house flies to apparent electrophoretic homogeneity was reported in G. D. Wheelock, et al., "Simultaneous Purification of a Cytochrome P-450 and Cytochrome b$_5$ from the House Fly *Musca domestica* L.", *Insect Biochem.*, 19:481–489 (1989), which is hereby incorporated by reference. This P450 runs as a single band at 54.3 kDa by SDS-PAGE, corresponding to a major band in LPR, and a phenobarbital-inducible band in wild-type (susceptible) flies. It has a carboxy ferrocytochrome absorbance maximum at 447 nm with no apparent peak at 420 (i.e., no denatured P450), has a high specific content (14.4 nmol/mg protein), and can be readily isolated in substantial quantities. Id. The N-terminal sequence of 15 amino acids for cytochrome P450$_{lpr}$ is disclosed in J. G. Scott, et al., "Characterization of a Cytochrome P450 Responsible for Pyrethroid Resistance in the Housefly," *Molecular Basis of Insecticide Resistance: Diversity Among Insects*, Symposium Series 505, C. J. Mullin and J. G. Scott, eds., American Chemical Society, Washington, D.C. (1992), which is hereby incorporated by reference. This sequence shares no homology with published P450 sequences. P450$_{lpr}$ appears to be a single cytochrome P450, because it cannot be resolved into multiple components chromatographically, immunologically, or electrophoretically. G. D. Wheelock, et al., "Immunological Detection of Cytochrome P450 from Insecticide Resistant and Susceptible House Flies (*Musca domestica*)," *Pestic. Biochem. Physiol.*, 38:130–39 (1990), which is hereby incorporated by reference. A polyclonal antiserum was raised in rabbits using purified cytochrome P450$_{lpr}$ protein as the antigen and was shown to be monospecific for cytochrome P450$_{lpr}$. This antiserum has proven extremely useful in the characterization of P450$_{lpr}$.

Immunological studies of insect P450s have shown limited homology with P450s from other classes. G. D. Wheelock, et al., "Expression of Cytochrome P-450$_{lpr}$ is Developmentally Regulated and Limited to House Fly," *J. Biochem. Toxicol.*, 6:239–246 (1991), which is hereby incorporated by reference, surveyed several animals for the presence of P450$_{lpr}$. Adult face flies, stable flies, and Drosophila all gave negative immuno-staining responses, as did larval Drosophila. Representatives of Hymenoptera (the honey bee and carpenter ant), Lepidoptera (the cabbage looper and tobacco hornworm), Orthoptera (the German cockroach), and Acari (the two spotted spider mite) did not immuno-stain. Phenobarbital induction of P450 was obtained in the face fly, stable fly, Drosophila adults, tobacco hornwork, German cockroach and honey bee. This induction did not produce immuno-stainable P450. P450 monooxygenase-mediated, insecticide-resistant arthropod strains tested include Hikone-R Drosophila, Dursban-R German cockroaches, and two spotted spider mites. Insecticide resistance did not confer expression of immunologically recognized cytochrome P450 in these arthropods. Id. Microsomes from rat or mouse liver were tested with anti-P-450$_{lpr}$ for cross-reactivity. No immuno-staining bands in blots from corn oil-treated, 3-methylchol-anthrene-treated or phenybarbital-treated rat liver microsomes were found. Additionally, no reaction was seen with corn oil/treated or benzo(e)pyrene-treated mouse liver microsomes. Id. It was concluded that P-450$_{lpr}$ is likely restricted to house flies due to the total lack of cross-reactivity to anti-P450$_{lpr}$ in any of the wide range of species tested.

Cytochrome P450$_{lpr}$ is expressed in both male and female adult LPR house flies. Id. Microsomes from males had a specific content of 0.53 nmol P450$_{lpr}$/total nmol of cytochrome P450 or 0.37 nmol P450$_{lpr}$/mg protein. Microsomes from female flies had 0.53 nmol P450$_{lpr}$/nmol P450 or 0.14 nmol P450$_{lpr}$/mg protein. Thus, P450$_{lpr}$ represented the same fraction of total P450 in both female and male microsomes but less on a per mg protein basis in females. Id. This agrees with previous reports examining the specific content of total cytochrome P450 (or cytochrome P450-dependent enzymatic activity) where only minor differences between adult male and female house flies have been found. M. Agosin, "Role of Microsomal Oxidation in Insecticide Degradation," *Comprehensive Insect Physiology, Biochemistry and Pharmacology*, Vol. 12, G. A. Kerkut and L. I. Gilbert, eds., Pergamon Press, Oxford (1985), which is hereby incorporated by reference.

It appears that cytochrome P450$_{lpr}$ is developmentally regulated in the LPR strain. G. D. Wheelock, et al., "Expression of Cytochrome P-450$_{lpr}$ is Developmentally Regulated and Limited to House Fly," *J. Biochem. Toxicol.*, 6:239–246 (1991), which is hereby incorporated by reference. P450$_{lpr}$ was present in adults of all ages, from 0–3 hr to 5–6 days post emergence as detected by SDS-PAGE immunoblotting. In contrast, microsomes from 1, 2, 3, 4, 5, and 6 day old LPR larvae revealed no immuno-staining material corresponding to P450$_{lpr}$. Id. P450$_{lpr}$ was expressed at barely detectable levels early in pupal development (i.e., between 24–48 hrs. after pupation), and was present at low levels in all pulal stages thereafter. M. E. McManus, et al., "Identification and Quantitation in Human Liver of Cytochrome P-450 Analogous to Rabbit Cytochrome P-450 Forms 4 and 6," *Xenobiotica*, 18:207–16 (1988), which is hereby incorporated by reference. Therefore, it appears that P450$_{lpr}$ is first synthesized in pupae, with significant P450$_{lpr}$ expression limited to adults, but it is not otherwise sex or age specific.

P450 isoforms are found in most tissues throughout the house fly abdomen. The relative abundance of P450$_{lpr}$ in abdominal tissues from adult female house flies is fat body proximal intestine>reproductive system. S. S. T. Lee, et al., "Tissue Distribution of Microsomal Cytochrome P450 Monooxygenases and Their Inducibility by Phenobarbital in the House Fly, *Musca domestica L.*," *Insect Biochem. Molec. Biol.*, 22:699–711 (1992), which is hereby incorporated by reference. Interestingly, P450$_{lpr}$ was found not only in tissues that have relatively high environmental exposure but also in the female reproductive system. This suggests that P450$_{lpr}$ may not be limited to xenobiotic detoxication but may also be important for other physiological functions.

The average amount of P450$_{lpr}$ in LPR microsomes, as a percentage of the total P450 was determined to be 68% by quantitative immuno-electrophoresis, G. D. Wheelock, et al., "Immunological Detection of Cytochrome P450 from Insecticide Resistant and Susceptible House Flies (*Musca domestica*)," *Pestic. Biochem. Physiol.*, 38:130–39 (1990), which is hereby incorporated by reference, suggesting that P450$_{lpr}$ was the major cytochrome P450 in microsomes from the pyrethroid-resistant LPR strain of the house fly. In microsomes from the insecticide-susceptible S+ strain, P450$_{lpr}$ was found to be a minority of the total cytochrome P450, comprising only 6.5% of the total. Id. A calculation from the specific contents results in an estimation of 44-fold higher levels of immunologically reactive cytochrome P450 in LPR microsomes compared to S+ microsomes. G. D. Wheelock, et al., "Expression of Cytochrome P-450$_{lpr}$ is Developmentally Regulated and Limited to House Fly," *J. Biochem. Toxicol.*, 6:239–246 (1991), which is hereby incorporated by reference. It appears that the immunoreactive proteins in the S+ and LPR strains are identical, because they are indistinguishable by electrophoretic, chromatographic, or immunological techniques and have the same N-terminal amino acid sequence. G. D. Wheelock, et al., "Immunological Detection of Cytochrome P450 from Insecticide Resistant and Susceptible House Flies (*Musca domestica*)," *Pestic. Biochem. Physiol.*, 38:130–39 (1990), Which is hereby incorporated by reference.

Microsomes from insecticide-resistant and susceptible house fly strains were evaluated for the presence of P450$_{lpr}$, and single immunoreactive bands were found in the resistant strains (i.e. LPR, Dairy, Kashiwagura, 3rd-Y, EPR, ASPRm, ASPRf), while the susceptible strains (i.e. aabys and S+) showed only weak reactions. Id. Additionally, cytochrome P450s were isolated and fractionated from the LPR, aabys, S+, Dairy, Kashiwagura, 3rd-Y, EPR, ASPRm, and ASPRf house fly strains using hydrophobic interaction and ion exchange HPLC. The fractionated P450s from the ion exchange step were assayed for immunoreactivity by quantitative immuno-electrophoresis. The results revealed a major cytochrome P450 peak of similar retention time associated with immunoreactivity for each strain. The immunoreactive fractions from the HPLC experiment all fused completely with P450$_{lpr}$, indicating immunological identity with P450$_{lpr}$. Id.

In addition to those references listed above, the following journal articles, all of which are hereby incorporated by reference, discuss studies of P450$_{lpr}$: G. D. Wheelock, et al., "Anti-P450$_{lpr}$ Antiserum Inhibits Specific Monooxygenase Activities in LPR House Fly Microsome," *The Journal of*

*Experimental Zoology,* 264:153–58 (1992); G. D. Wheelock. et al., "The Role of Cytochrome P450$_{lpr}$ in Deltamethrin Metabolism by Pyrethroid-Resistant and Susceptible Strains of House Flies," *Pestic. Biochem. & Physiol.,* 43:67–77 (1992).; S. S. T. Lee, et al., "In Vitro Induction of Microsomal Cytochrome P-450 Monooxygenases by Phenobarbital in Fat Bodies of Adult House Fly, *Musca domestica L.,*" *Insect Biochem. Molec. Biol.,* 22 (7): 691–98 (1992); R. Hatano, et al., "Anti-P450$_{lpr}$ Antiserum Inhibits the Activation of Chlorpyrifos to Chlorpyrifos Oxan in House Fly Microsomes," *Pestic. Biochem. & Physiol.,* 45:228–33 (1993); J. G. Scott, "The Cytochrome P450 Microsomal Monooxygenases of Insects: Recent Advances," *Rev. Pestic. Toxicol.,* Vol. 2, R. M. Roe et. al., editors (1993); and J. G. Scott, et al., "Purification and Characterization of a Cytochrome P-450 From Insecticide Susceptible and Resistant Strains at Housefly *Musca domestica L.,* Before and After Phenobarbital Exposure," *Arch. Insect Biochem. & Physiol.,* 24:1–19 (1993).

SUMMARY OF THE INVENTION

The present invention relates to an isolated DNA molecule encoding a cytochrome P450$_{lpr}$ polypeptide as well as an isolated cytochrome P450$_{lpr}$ polypeptide itself. The DNA molecule can be inserted as a heterologous DNA in an expression vector forming a recombinant DNA expression system for producing the polypeptide. Likewise, the heterologous DNA, usually inserted in an expression vector to form a recombinant DNA expression system, can be incorporated in a host cell for expression of cytochrome P450$_{lpr}$ polypeptide.

The DNA molecule of the present invention can be utilized in a variety of ways. According to one use, insect larvae can be treated with a vector containing the DNA molecule of the present invention to achieve insect control. Alternatively, adult insects can be controlled by treating them with a vector comprising the DNA molecule of the present invention together with an insecticide. The DNA molecule of the present invention can also be used in a bioremediation process by applying a vector comprising that DNA molecule to an insecticide. Yet another aspect of the present invention involves transforming crop plants with the DNA molecule encoding cytochrome P450$_{lpr}$ polypeptide to reduce their sensitivity to pesticides.

BRIEF DESCRIPTION OF THE DRAWINGS

FIG. 2 shows the cDNA (SEQ. ID. No. 1) and deduced protein (SEQ. ID. No. 2) sequences of P450$_{lpr}$. The bases are numbered from the translation initiation site as +1. Putative polyadenylation signals and the amino acid sequences primarily determined from P450$_{lpr}$ polypeptides are underlined. EcoRI site and the invariant or highly conserved residues in all the P450 proteins are doubly underlined. The intron insertion sites in the corresponding genomic DNA are shown with tentative numbers on the cDNA sequence.

FIG. 4 shows the alignment of housefly P450$_{lpr}$ with P450VI family insect members and a P450III family member. A colon denotes a residue shared among all the sequences in alignment; a dot denotes a residue shared among four sequences. Numbering on the alignment shows lpr residue positions. Numbering in parenthesis shows alignment frame positions.

FIG. 5 depicts a comparison of the amino sequence for cytochrome P450$_{lpr}$ and the corresponding amino acid sequence for susceptible house flies.

FIGS. 6A–6D depict a comparison of the nucleotide sequence for cytochrome P450$_{lpr}$ and the corresponding nucleotide sequence for susceptible house flies.

DETAILED DESCRIPTION OF THE INVENTION

Figure 1:
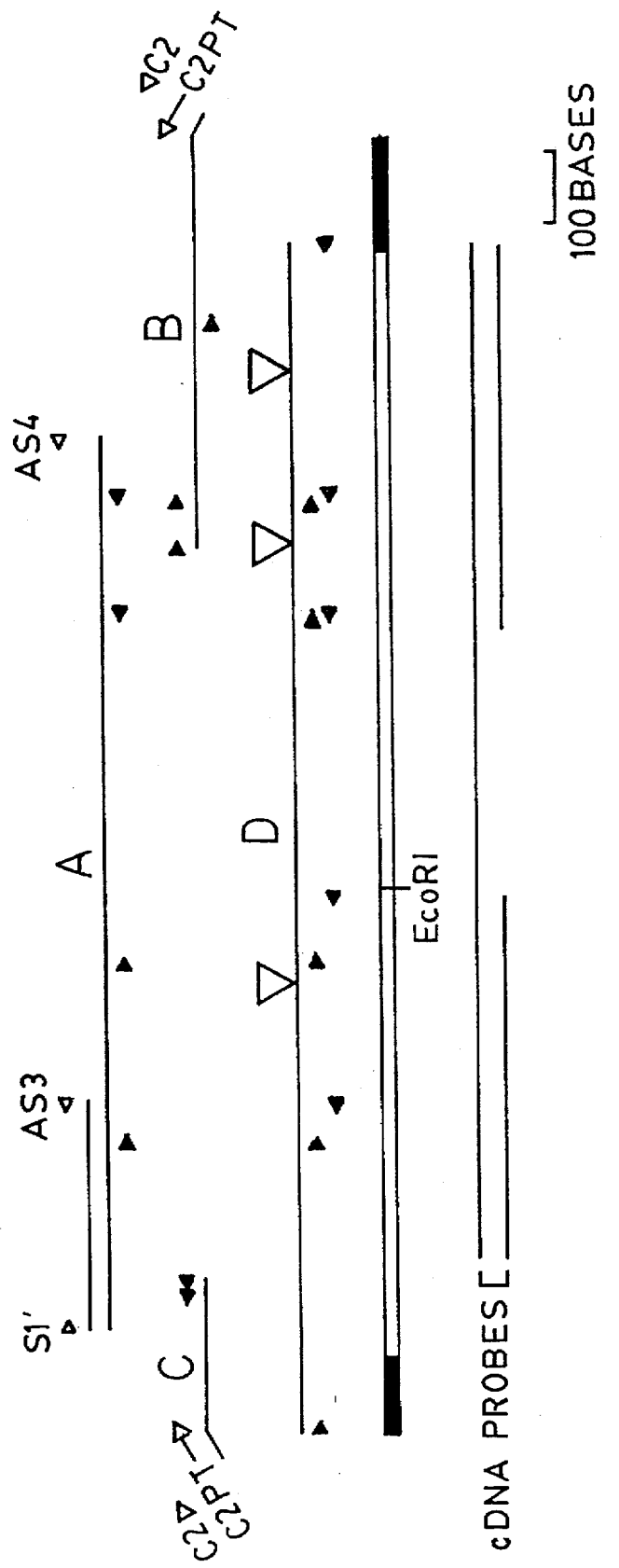
FIG. 1 shows an in vitro cloning strategy by PCR. cDNA parts amplified from center region, A; downstream, B; upstream, C; a cDNA region examined for intron insertions in the corresponding genomic DNA, D. The arrow heads presented on A-C lines shows primers used for amplification of each cDNA part; the arrow heads under A, B, D shows the primers used for primer walking or for differential size screening of intron-involving PCR products from genomic DNA; triangles present intron insertion sites in the corresponding structure gene sequence. White and black bars present cDNA coding region and untranslated regions, respectively. The sequences of named primers are described infra in Table 1.

The present invention relates to an isolated DNA molecule encoding for cytochrome P450$_{lpr}$ polypeptide. This DNA molecule comprises the nucleotide sequence corresponding to SEQ. ID. No. 1 as follows:

```
ATGTTGTTATTACTGCTGCTGATTGTGGTGACGACCCTCTATATCTTTGCCAAACTCCAT

TATACGAAATGGGAACGTTTGGGTTTCGAATCGGATAAGGCCACCATACCCCTGGGCTCA

ATGGCAAAGGTATTCCACAAGGAACGGCCATTTGGCCTGGTTATGTCCGACATATATGAC

AAATGCCACGAGAAGGTGGTGGGCATTTATTTGTTCTTCAAGCCGGCCCTACTGGTACGT

GATGCCGAATTGGCGAGACAAATTTTGACCACGGATTTTAATAGCTTCCACGATCGTGGC

CTCTATGTGGATGAGAAAAATGATCCAATGTCGGCGAATCTTTTCGTGATGGAGGGTCAA

TCATGGCGTACGCTGAGAATGAAATTGGCCCCCTCGTTTTCGTCGGGTAAACTCAAGGGG
```

-continued

```
ATGTTCGAAACGGTCGATGATGTGGCGGATAAATTAATAAATCACTTGAATGAGCGCTTG

AAGGATGGCCAGACGCATGTTTTGGAAATCAAGAGTATTTTGACCACCTATGCTGTCGAC

ATCATTGGTTCGGTGATATTCGGCCTGGAAATCGATAGTTTCACCCATCCGGACAATGAA

TTTCGTGTCTTAAGTGATCGTCTATTTAACCCAAAGAAGTCGACAATGTTGGAGAGAATT

CGCAATTTATCAACCTTTATGTGTCCACCACTTGCCAAACTCTTGTCGCGCCTTGGTGCC

AAGGATCCGATAACATATCGCCTGCGCGACATCGTGAAACGGACGATAGAATTTCGCGAA

GAAAAGGGCGTTGTACGCAAAGATCTTCTCCAGCTATTTATACAACTCAGAAATACTGGA

AAAATTTCCGATGACAATGACAAGCTATGGCATGACGTTGAGTCGACGGCGGAAAATCTC

AAAGCCATGTCTATCGATATGATTGCCTCCAATTCATTCCTATTCTATATTGCCGGTTCG

GAAACAACGGCGGCCACAACATCATTTACCATCTATGAATTGGCCATGTATCCGGAAATT

TTGAAAAAGGCCCAATCTGAGGTGGATGAGTGCCTGCAAAGGCATGGTCTCAAGCCGCAG

GGACGGCTGACATATGAGGCAATACAGGATATGAAATATTTGGATTTGTGTGTTATGGAA

ACCACCCGCAAATACCCCGGCCTGCCGTTTTTGAATCGCAAATGCACTCAGGATTTCCAA

GTACCCGACACAAAACTGACCATACCAAAGGAAACGGGAATTATCATCTCCTTGTTGGGC

ATCCATAGAGACCCACAGTATTTCCCCCAACCCGAGGATTATAGGCCAGAACGCTTTGCC

GATGAGAGCAAGGATTATGATCCAGCGGCATATATGCCTTTTGGAGAGGGTCCAAGGCAT

TGTATTGCTCAACGCATGGGCGTTATCAATTCCAAGGTAGCCTTGGCCAAAATATTGGCC

AATTTTAATATTCAACCAATGCCCCGCCAAGAAGTTGAGTTCAAATTCCATTCAGCTCCT

GTTCTGGTGCCAGTAAATGGTCTCAATGTGGGCCTGTCGAAGAGGTGGTGA
```

The DNA molecule, corresponding to SEQ. ID. No. 1, encodes for the deduced cytochrome P450$_{tpr}$ polypeptide or protein which corresponds to SEQ. ID. No. 2 as follows:

Met Leu Leu Leu Leu Leu Leu Ile Val Val Thr Thr Leu Tyr Ile
Phe Ala Lys Leu His Tyr Thr Lys Trp Glu Arg Leu Gly Phe Glu

Ser Asp Lys Ala Thr Ile Pro Leu Gly Ser Met Ala Lys Val Phe
His Lys Glu Arg Pro Phe Gly Leu Val Met Ser Asp Ile Tyr Asp

Lys Cys His Glu Lys Val Val Gly Ile Tyr Leu Phe Phe Lys Pro
Ala Leu Leu Val Arg Asp Ala Glu Leu Ala Arg Gln Ile Leu Thr

Thr Asp Phe Asn Ser Phe His Asp Arg Gly Leu Tyr Val Asp Glu
Lys Asn Asp Pro Met Ser Ala Asn Leu Phe Val Met Glu Gly Gln

-continued

Ser Trp Arg Thr Leu Arg Met Lys Leu Ala Pro Ser Phe Ser Ser
Gly Lys Leu Lys Gly Met Phe Glu Thr Val Asp Asp Val Ala Asp

Lys Leu Ile Asn His Leu Asn Glu Arg Leu Lys Asp Gly Gln Thr
His Val Leu Glu Ile Lys Ser Ile Leu Thr Thr Tyr Ala Val Asp

Ile Ile Gly Ser Val Ile Phe Gly Leu Glu Ile Asp Ser Phe Thr
His Pro Asp Asn Glu Phe Arg Val Leu Ser Asp Arg Leu Phe Asn

Pro Lys Ser Thr Met Leu Glu Arg Ile Arg Asn Leu Ser Thr
Phe Met Cys Pro Leu Ala Lys Leu Leu Ser Arg Leu Gly Ala

Lys Asp Pro Ile Thr Tyr Arg Leu Arg Asp Ile Val Lys Arg Thr
Ile Glu Phe Arg Glu Glu Lys Gly Val Val Arg Lys Asp Leu Leu

-continued

Gln Leu Phe Ile   Gln Leu Arg Asn Thr Gly Lys Ile   Ser <u>Asp Asp</u>

<u>Asn Asp Lys Leu</u> Trp His Asp Val Glu Ser Thr Ala Glu Asn Leu

Lys Ala Met Ser Ile   Asp Met Ile   Ala Ser Asn Ser Phe Leu Phe

Tyr Ile   Ala Gly Ser Glu Thr Thr Ala Ala Thr Thr Ser Phe Thr

Ile   Tyr Glu Leu Ala Met Tyr Pro Glu Ile   Leu Lys Lys Ala Gln

Ser Glu Val Asp Glu Cys Leu Gln Arg His Gly Leu Lys Pro Gln

Gly Arg Leu Thr Tyr Glu Ala Ile   Gln Asp Met Lys Tyr Leu Asp

Leu Cys Val Met Glu Thr Thr Arg Lys Tyr Pro Gly Leu Pro Phe

Leu Asn Arg Lys Cys Thr Gln Asp Phe Gln Val Pro Asp Thr Lys

Leu Thr Ile   Pro Lys <u>Glu Thr Gly Ile   Ile   Ile   Ser Leu Leu Gly</u>

<u>Ile   His Arg Asp</u> Pro Gln Tyr Phe Pro Gln Pro Glu Asp Tyr Arg

<u>Pro Glu</u> Arg Phe Ala Asp Glu Ser Lys Asp Tyr Asp Pro Ala Ala

Tyr Met Pro Phe Gly Glu Gly Pro Arg His Cys Ile   Ala Gln Arg

Met Gly Val Ile   Asn Ser Lys Val Ala Leu Ala Lys Ile   Leu Ala

Asn Phe Asn Ile   Gln Pro Met Pro Arg Gln Glu Val Glu Phe Lys

Phe His Ser Ala Pro Val Leu Val Pro Val Asn Gly Leu Asn Val

Gly Leu Ser Lys Arg Trp TGA

In the amino acid sequence designated as SEQ. ID. No. 2, the underlined sequences correspond to peptides known from sequencing digested protein. These sequences are separately denominated as SEQ. ID. Nos. 3–7 as follows:

SEQ. ID. No. 3:

Met Leu Leu Leu Leu Leu Leu Ile   Val Val Thr Thr Leu Tyr Ile

Phe Ala Lys Leu

SEQ. ID. No. 4:

Gly Leu Tyr Val Asp Glu Lys Asn Asp Pro Met Ser Ala Asn Leu

Phe Val Met Glu Gly Gln

SEQ. ID. No. 5:

Asp Asp Asn Asp Lys Leu

SEQ. ID. No. 6:

Glu Thr Gly Ile   Ile   Ile   Ser Leu Leu Gly Ile   His

SEQ. ID. No. 7:

Pro Gln Tyr Phe Pro Gln Pro Glu Asp Tyr Arg Pro Glu

The protein or polypeptide of the present invention is preferably produced in purified form by conventional techniques. Typically, the protein or polypeptide of the present invention is secreted into the growth medium of recombinant E. coli. To isolate the protein, the E. coli host cell carrying a recombinant plasmid is propagated, homogenized, and the homogenate is centrifuged to remove bacterial debris. The supernantant is then subjected to sequential ammonium sulfate precipitation. The fraction containing the protein of the present invention is subjected to gel filtration in an appropriately sized dextran or polyacrylamide column to separate the proteins. If necessary, the protein fraction may be further purified by HPLC.

The DNA molecule encoding the cytochrome $P450_{ipr}$ polypeptide can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, New York (1982), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promotors differ from those of procaryotic promotors. Furthermore, eucaryotic promotors and accompanying genetic signals may not be recognized in or may not function in a procaryotic system, and, further, procaryotic promotors are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promotors vary in their "strength" (i.e. their ability to promote transcription). For the purposes of expressing a cloned gene, it is desirable to use strong promotors in order to obtain a high level of transcription and, hence, expression of the gene. Depending upon the host cell system utilized, any one of a number of suitable promotors may be used. For instance, when cloning in *E. coli*, its bacteriophages, or plasmids, promotors such as the T7 phage promoter, lac promotor, trp promotor, recA promotor, ribosomal RNA promotor, the $P_R$ and $P_L$ promotors of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promotors produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno (SD) sequence about 7–9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding cytochrome $P450_{lpr}$ polypeptide has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, and the like.

Cytochrome $P450_{lpr}$ is an enzyme capable of metabolizing insecticides. $P450_{lpr}$ detoxifies pyrethroids and activates organophosphate insecticides. These are the two most widely used classes of insecticides worldwide. Possible applications of the cytochrome $P450_{lpr}$ DNA molecule and polypeptide sequences of the present invention include: 1) the expression of $P450_{lpr}$ for use as an insecticide; 2) expression of $P450_{lpr}$ in an appropriate vector for use as a synergist for organophosphate insecticides; 3) expression of $P450_{lpr}$ in an appropriate vector as a bioremediation agent for the clean up of pyrethroid insecticide residues; and 4) engineering the $P450_{lpr}$ gene into plants to reduce phytotoxicity of insecticides.

One aspect of the present invention is directed to a method of insect control where insect larvae are treated with a vector containing the DNA molecule of the present invention. It has been found that cytochrome $P450_{lpr}$ is a developmentally regulated protein that is expressed in adults, but not in larval houseflies. This suggests that the $P450_{lpr}$ protein is strictly controlled (i.e., not expressed) in larvae in order to allow them to develop normally. Thus, cloning the $P450_{lpr}$ DNA molecule into a vector, infecting larvae with that vector, and expressing the $P450_{lpr}$ protein in infected larvae would be useful as an insecticide. More particularly, such expression of the DNA molecule encoding $P450_{lpr}$ protein would either kill larvae or radically disrupt their development. Additionally, because the protein is house fly specific, it may be lethal to other insects if expressed.

A particularly suitable vector for infecting insect larvae is the insect-specific baculovirus. When using the baculovirus system to infect larvae, it is first necessary to clone the DNA molecule coding for cytochrome $P450_{lpr}$ polypeptide into a baculovirus transfer vector. The baculovirus transfer vector and *Autographa californica* nuclear polyhedrosis virus genomic DNA are then used to coinfect host insect cells. Suitable insect cells for such transfection are Sf-9 or Sf-21 insect cells. A recombinant baculovirus can then be recovered and used to infect insect larvae in accordance with the above-described method.

Vectors containing the DNA molecule encoding for cytochrome $P450_{lpr}$ polypeptide can be applied directly or indirectly to insect larvae as a spray. For example, the polypeptide can be used to treat plants, soil or other habitat. It may also be used in conjunction with an attractant (e.g., a pheromone), particularly where the surface of application is not a food source to lure adult female insects to that surface where they deposit their eggs. The vector containing DNA encoding for cytochrome $P450_{lpr}$ polypeptide then infects either the eggs or the resulting larvae so that that DNA molecule is incorporated in the eggs or larvae. Subsequent expression of cytochrome $P450_{lpr}$ acts against propagation of the eggs or larvae.

Additionally, as discussed more fully infra, a gene encoding for the polypeptide can be incorporated in a plant, which would normally serve as an insect food source. In this embodiment, the expressed polypeptide would serve as an insecticide to insects consuming the plant.

In another aspect of the present invention, a vector containing the DNA molecule encoding for cytochrome $P450_{lpr}$ polypeptide is used to treat adult insects as part of an insect control procedure. In this embodiment of the present invention, the vector is used together with an organophosphate insecticide, because it has been found that cytochrome $P450_{lpr}$ polypeptide is effective in achieving activation of such insecticides. See R. Hatano, et al., "Anti-$P450_{lpr}$ Antiserum Inhibits the Activation of Chlorphyrifos to Chlorphyrifos Oxon in Housefly Microsomes", *Pestic. Biochem. and Physiol.*, 45:228–33 (1993), which is hereby incorporated by reference. As a result, insects which express high levels of $P450_{lpr}$ are more likely to be sensitive to organophosphate insecticides. This would allow lower concentrations of the organophosphate insecticides to be used and would be useful as a strategy for control of organophosphate resistance in insects.

Suitable organophosphate insecticides for use in conjunction with the present invention include (but are not limited): parathion, malathion, azinphosmethyl, diazinon, chlorphyrifos, terbufos, and fenitrothion. Generally, organophosphate insecticides are used at levels of 0.2 to 60 pounds per acre. The vector containing the DNA molecule of the present invention can be utilized in conjunction with an organophosphate insecticide in the form of a spray, powder, or with an attractant. Again, this regime for controlling adult insects is particularly adaptable to use with the baculovirus vector, as described above.

In yet another aspect of the present invention, a vector containing the DNA molecule encoding for cytochrome $P450_{lpr}$ polypeptide can be applied to insecticide spills as part of a method of bioremediation. Microorganisms can be extremely useful as agents for clean-up of environmental problems, including pesticides spills. Development of suitable microorganisms involves either selecting microorganisms with a bioremediation trade or by introducing a gene into microbes to engender them with that ability. By introducing the DNA molecule encoding for cytochrome $P450_{lpr}$ polypeptide into an appropriate vector, it is possible to achieve bioremediation of insecticide residues. Suitable vectors are non-pathogenic bacteria.

In yet another aspect of the present invention, the DNA molecule encoding cytochrome $P450_{lpr}$ can be used to transform crop plants in order to reduce their sensitivity to pesticides. If crops are sensitive to certain pesticides, the types of materials used to control insects in conjunction with such crops may be severly limited. There has been a great deal of recent activity in the agrochemical industry to develop genes that confer tolerance to pesticides. As a result, compounds that might not normally be used in conjunction with a given crop due to phytotoxicity problems can be useful. Similarly, since cytochrome $P450_{lpr}$ is known to be useful in breaking down pesticides, expression of a gene encoding for that protein within plants will confer protection against pesticide phytotoxicity.

The isolated DNA molecule of the present invention can be utilized to confer protection against pesticide phytotoxicity for a wide variety of plants, including gymnosperms, monocots, and dicots. Although the gene can be inserted into any plant falling within these broad classes, it is particularly useful in crop plants, such as rice, wheat, barley, rye, corn, potato, carrot, sweet potato, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum, and sugarcane. The present invention may also be used in conjunction with non-crop plants, including *Arabidopsis thaliana*.

The expression system of the present invention can be used to transform virtually any crop plant cell under suitable conditions. Cells transformed in accordance with the present invention can be grown in vitro in a suitable medium to confer protection against pesticide phytotoxicity. This protein can then be harvested or recovered by conventional purification techniques. The isolated protein can be applied to plants (e.g., by spraying) as a topical application to impart protection against pesticide phytotoxicity. Alternatively, transformed cells can be regenerated into whole plants such that this protein imparts protection against pesticide phytotoxicity to the intact transgenic plants. In either case, the plant cells transformed with the recombinant DNA expression system of the present invention are grown and caused to express that DNA in the cells to confer protection against pesticide phytotoxicity on them.

One technique of transforming plants with the DNA molecule in accordance with the present invention is by contacting the tissue of such plants with an inoculum of a bacteria transformed with a vector comprising a gene in accordance with the present invention which confers pesticide resistance. Generally, this procedure involves inoculating the plant tissue with a suspension of bacteria and incubating the tissue for 48 to 72 hours on regeneration medium without antibiotics at 25°–28° C.

Bacteria from the genus Agrobacterium can be utilized to transform plant cells. Suitable species of such bacterium include *Agrobacterium tumefaciens* and *Agrobacterium rhizogenes*. *Agrobacterium tumefaciens* (e.g., strains LBA4404 or EHA105) is particularly useful due to its well-known ability to transform plants. Another approach to transforming plant cells with a gene which confers protection against pesticide phytotoxicity involves propelling inert or biologically active particles at plant tissues cells. This technique is disclosed in U.S. Pat. Nos. 4,945,050, 5,036,006, and 5,100,792 all to Sanford et al., which are hereby incorporated by reference.

As noted above, in addition to having protection against pesticide phytotoxicity, plants transformed with a gene encoding for the cytochrome $P450_{lpr}$ polypeptide will be useful in killing insects when this polypeptide is produced.

EXAMPLES

The following examples illustrate, but are not intended to limit, the present invention.

Example 1

Strain

The LPR strain of the housefly was originally collected in 1982 from a dairy in New York, and selected with permethrin for 22 generations. The LPR attained to a high and stable level of resistance to pyrethroid insecticides with a phenoxybenzyl alcohol moiety (e.g. 6,000-fold permethrin resistance and >10,000-fold deltamethrin resistance). See J. G. Scott, et al., "Mechanisms Responsible for High Levels of Permethrin Resistance in the House Fly," *Pestic. Sci.*, 17:195–206 (1986), which is hereby incorporated by reference. The flies were reared in a standard medium, and 0 day old adults were used without further treatment for RNA extraction.

Example 2

Oligopeptide Sequencing

The cytochrome $P450_{lpr}$ protein was purified from microsome of adult abdomens by HPLC, G. D. Wheelock, et al., "Simultaneous Purification of a Cytochrome P-450 and Cytochrome $b_5$ from the House Fly *Musca domestica* L.", *Insect Biochem.*, 19:481–489 (1989), which is hereby incorporated by reference, as a single immunoreactive protein. The isolated protein was cleaved with trypsin, and the resulting oligopeptides were sequenced on an Applied Biosystems, Model 470. Three of the 4 determined polypeptide sequences were utilized for degenerate oligonucleotide designation.

Example 3 cDNA Amplification

RNA was extracted from 15 abdomens by the guanidium isothiocyanate-hot phenol method. Poly(A)-RNA was screened by a Oligotex® Qiagen, Chatsworth, Calif. batch treatment method. The first-strand cDNA was synthesized with Molony murine leukemia virus ("M-MLV") reverse transcriptase (Perkin-Elmer, Norwalk, Conn.), 1 µg of poly (A)-enriched RNA, and an antisense primer or a 5'-anchored oligo(dT)$_{16}$ primer, at 42° C. for 1 hr. This step was followed by heat-inactivation and polymerase chain reaction ("PCR") with 0.2 mM each of a primer set in 100 µl reaction volume. Each reaction cycle (95° C. for 0.5 min, 55° C. for 1 min, and 72° C. for 2 min) was repeated 25–30 times and followed by the final elongation step (72° C. for 7 min).

Example 4

Genomic DNA Amplification

DNA was extracted from adult flies by proteinase K and phenol-chlorform treatments. The precipitated nucleic acids were treated with RNase A, and the initial extraction steps were repeated. One microgram DNA was used as a PCR template in a 100 µl reaction volume.

Example 5

Terminal Transferase Reaction

The first-strand cDNA synthesized with M-MLV reverse transcriptase was treated with phenol-chlorform and precipitated 4 times with Ethachinmate (an acrylamide DNA-carrier, Nippon Gene, Tokyo, Japan) by ethanol precipitation. dATPs were tailed to the 3' end of first-strand cDNA with terminal deoxynucleotidyl transferase (GIBCO BRL, Gaithersburg, Md.) in the condition described by the manufacturer. The cDNA was extracted by phenol-chlorform treatment and precipitated.

Example 6

DNA Sequencing

The first PCR product was separated by agarose gel electrophoresis. A DNA band was extracted from the gel, purified by QIAEX® matrix protocol (Qiagen, Chatsworth, Calif.) and used as a template for a second PCR step with the same or internal primers. To the second PCR product, concentrated through ethanol precipitation, the same gel extraction procedures were applied. Double-stranded PCR product was directly sequenced by the dideoxynucleotide chain termination method with [@-35S]thiodATP and SEQUENASE® kit (United States Biochemical Corp., Cleveland, Ohio) according to the manufacturers protocol, which is hereby incorporated by reference, except for, the addition of dimethylsulfoxide at a final concentration of 10% (v/v) to the reaction solution, and DNA denaturation at 95° C. for 3 min followed by quenching on dry ice.

Example 7

Southern Hybridization

Genomic DNA fragments after digestion with EcoRI were separated by agarose gel electrophoresis, and blotted on nylon membrane. Pure PCR product from $P450_{lpr}$ cDNA coding region was labelled with [@-32P]dCTP by random priming method, and hybridized on the membrane with sheared salmon DNA in QUICK HYB® solution (Strategene, LaJolla, Calif.). Hybridization and washing followed high stringency condition.

Example 8

In Vitro Cloning Strategies

To obtain cDNA clones which covers coding region, cDNA was synthesized and amplified by reverse transcription-mediated polymerase chain reaction (RT-PCR), separated into 3 parts. The sequences of the key primers used for RT-PCR are shown in Table 1, while their based amino acid sequences and the priming sites are mapped in FIG. 1.

TABLE 1

Oligonculeotides Used for cDNA Synthesis and Amplification

| Names | Oligonucleotide Sequences | Corresponding polypeptide sequences |
|---|---|---|
| S1'* | 5'-AC(CG)(TC)T(GC)TA(TC)AT(TC)TT(TC)GCCAA-3' (SEQ. ID. No. 8) | TLYIFAK (SEQ. ID. No. 13) |
| AS3# | 5'-(TC)TG(AG)CC(TC)TCCAT(CATG)AC(AG)AA-3' (SEQ. ID. No. 9) | FVMEGQ (SEQ. ID. No. 14) |
| AS4# | 5'-TC(ATC)GG(TC)TG(CTAG)GG(AG)AA(AG)TA(TC)TG-3' (SEQ. ID. No. 10) | QYFPQP (SEQ. ID. No. 15) |
| C2 | 5'- TAATACGACTCACTATAGGGAGA-3' | |

TABLE 1-continued

Oligonucleotides Used for cDNA Synthesis and Amplification

| Names | Oligonucleotide Sequences | Corresponding polypeptide sequences |
|---|---|---|
| C2PT | (SEQ. ID. No. 11)<br>5'- TAATACGACTCACTATAGGGAGATTTTTTTTTTTTTTTT-3'<br>(SEQ. ID. No. 12) | |

Nucleotides in parentheses present mixed incorporation.
*Sense primer.
Antisense primers.

First, 2 overlapping internal sequences from coding region were amplified with the degenerate primers based on P450$_{lpr}$ polypeptide sequences (FIG. 1A); the longer PCR product of 1.4 kilobase pairs ("kbp") was obtained with S1 and AS4 primer set; the shorter one was obtained with S1 and AS3. Here we denote that a sense primer S1 is designed from N-terminal sequence. A serial sequence of 1.3 kb was obtained from these products followed by subsequent primer walking. Second, a cDNA sequence encoding C-terminal region was amplified with the first-strand cDNA primed by the 5'-anchored poly(dT) oligonucleotide, C2PT (FIG. 1B); this cDNA was amplified by single side-nested PCR with coding region specific sense primers (upstream from AS4, sequences not shown) and the anchor specific C2 primer. A sequence of 160 bases was obtained with this product. Third, a cDNA sequence encoding N-terminus was amplified with the first-strand cDNA that was primed by an antisense primer (downstream from S1, sequence not shown) and tailed at the 3' end by poly-(dA) by terminal deoxynucleotidyl transferase reaction (FIG. 1C). This cDNA was amplified following the analogous nested PCR and a sequence of 530 bases was determined.

Example 9

Nucleotide Sequence

A serial sequence of 1816 bases (FIG. 2) was obtained from the 3 in vitro cDNA clones. This sequence has an open reading frame of 1548 bases, coding a 516 residues (Mr 59,182). This agrees with a molecular mass of the purified protein. See G. D. Wheelock, et al., "Simultaneous Purification of a Cytochrome P-450 and Cytochrome b$_5$ from the House Fly Musca domestica L", Insect Biochem. 19:481–489 (1989), which is hereby incorporated by reference. Putative polyadenylation signals, AUUUA (SEQ. ID. No. 16) and AAUAAA (SEQ. ID. No. 17), appear twice within the 3'-untranslated region, although no poly(A) was observed.

Figure 2:
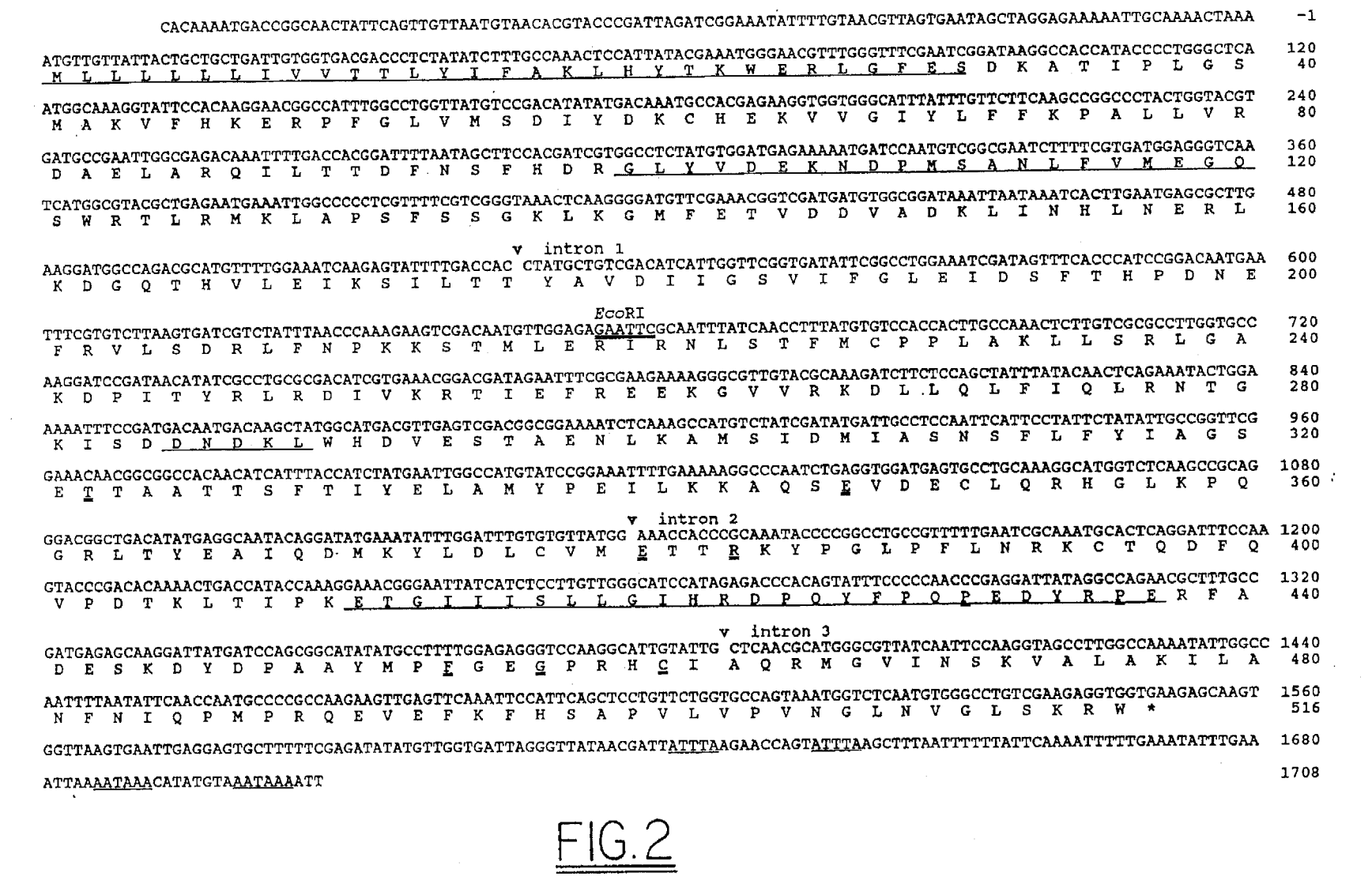
Figure 3:
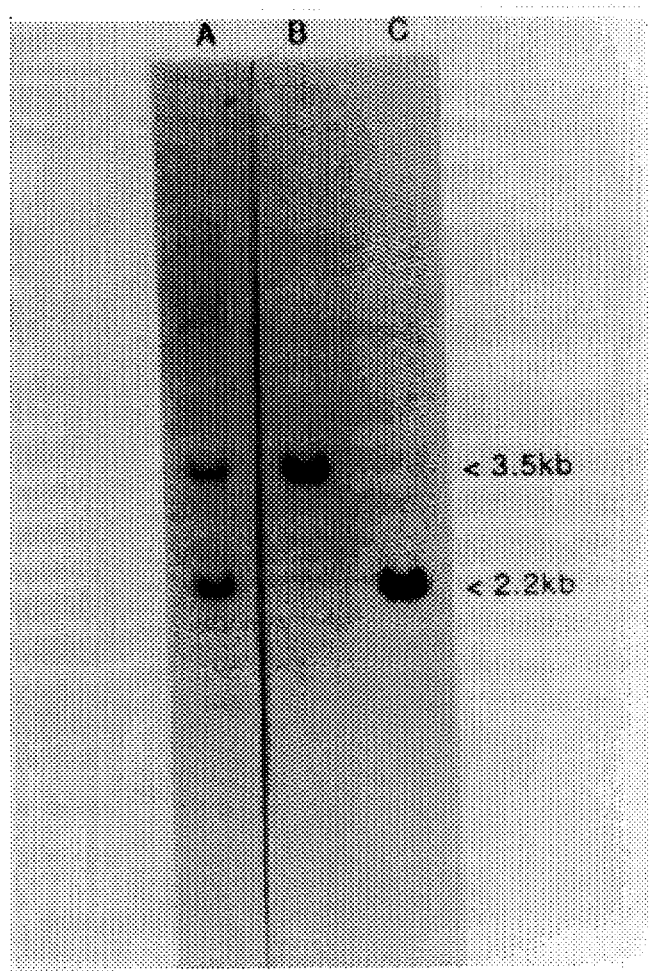
FIG. 3 shows the genomic Southern hybridization of LPR DNA fragments. Autoradiography A, B, and C show an EcoRI DNA blot hybridized to each of the 3 cDNA probes, upstream and downstream from, and encompassing, a unique EcoRI site in the P450$_{lpr}$ cDNA sequence, respectively. The arrangement of the cDNA probes are shown in FIG. 1. EcoRI fragments of 2.2 and 3.5 kbp were oriented in this order.

Three cDNA probes upstream and/or downstream from an unique EcoRI site in the obtained cDNA sequence (FIGS. 1 and 2) were used for orienting the genomic DNA fragments from LPR flies. Two EcoRI DNA fragments of 2.2 and 3.3 kbp, hybridized with upstream and downstream cDNA probes, respectively, and they were oriented in this order (FIG. 3). This result also shows that the DNA sequence obtained was derived from an identical gene sequence, as well as the involvement of experimentally obtained 4 polypeptide sequences in the deduced protein sequence (FIG. 2).

Intron insertion was analyzed by differential size screening of paired PCR products which were derived from cDNA and genomic DNA templates with common primer sets, followed by the subsequent sequencing of the genomic DNA-PCR products (FIG. 1D). A total of 5 pairs of PCR products in screening covers a 5'-untranslated region and most of the coding region (cDNA bases –88 to 1544) with serial overlaps. Three introns with 74, 66, and 64 bases have split within the coding sequence in this order (for insertion site, see FIG. 2) and they were tentatively numbered as intron 1, and 3, respectively.

Intron 1 sequence is:

GTAAGTACTCATCGTTGAGAGAATTGTAAGAAGTTTTGAATTTTACTTTTAATAAAATGT

TCTTCTTCCCCCAG (SEQ. ID. No. 18).

Intron 2 is:

GTAAGAGGGGAAATTTTGAAATTGTTTTTTTTTTATTTTCTAATTATTGCATGTTTTG

TTGTAG (SEQ. ID. No. 19).

Intron 3 is:

GTGAGATGTTGAAAGGGGAGCTTCATTAAATTCTGAATATTAATTTTGTATTTTTTTCC

ACAG (SEQ. ID. No. 20).

Each sequence had a canonical 5'-GT and AG-3' terminal bases.

Example 10

Comparison with Other P450 Sequences

The cytochrome P450$_{lpr}$ sequence involves a FXXGXXXC sequence (SEQ. ID. No. 21) near the N-terminus (FIG. 2). In SEQ. ID. No. 21, X can be any amino acid. This sequence is invariant in P450 super gene family members and the best key for characterizing P450 sequences, and Cys-461 in this sequence is known as the fifth ligand to heme. Also Gly-455, Arg-459, Ala-463, Gly-467, and Ans-470 in or C-distal from this invariant residue appear to be major or already identified residues at the conserved positions within heme-binding region. The N-terminal region of the lpr sequence is highly hydrophobic over first 19 residues that agrees with a common feature of N-terminal region of microsomal P450s as an membrane-anchor signal. The other conserved or possible functional regions involved in the lpr are discussed infra.

Figure 4:
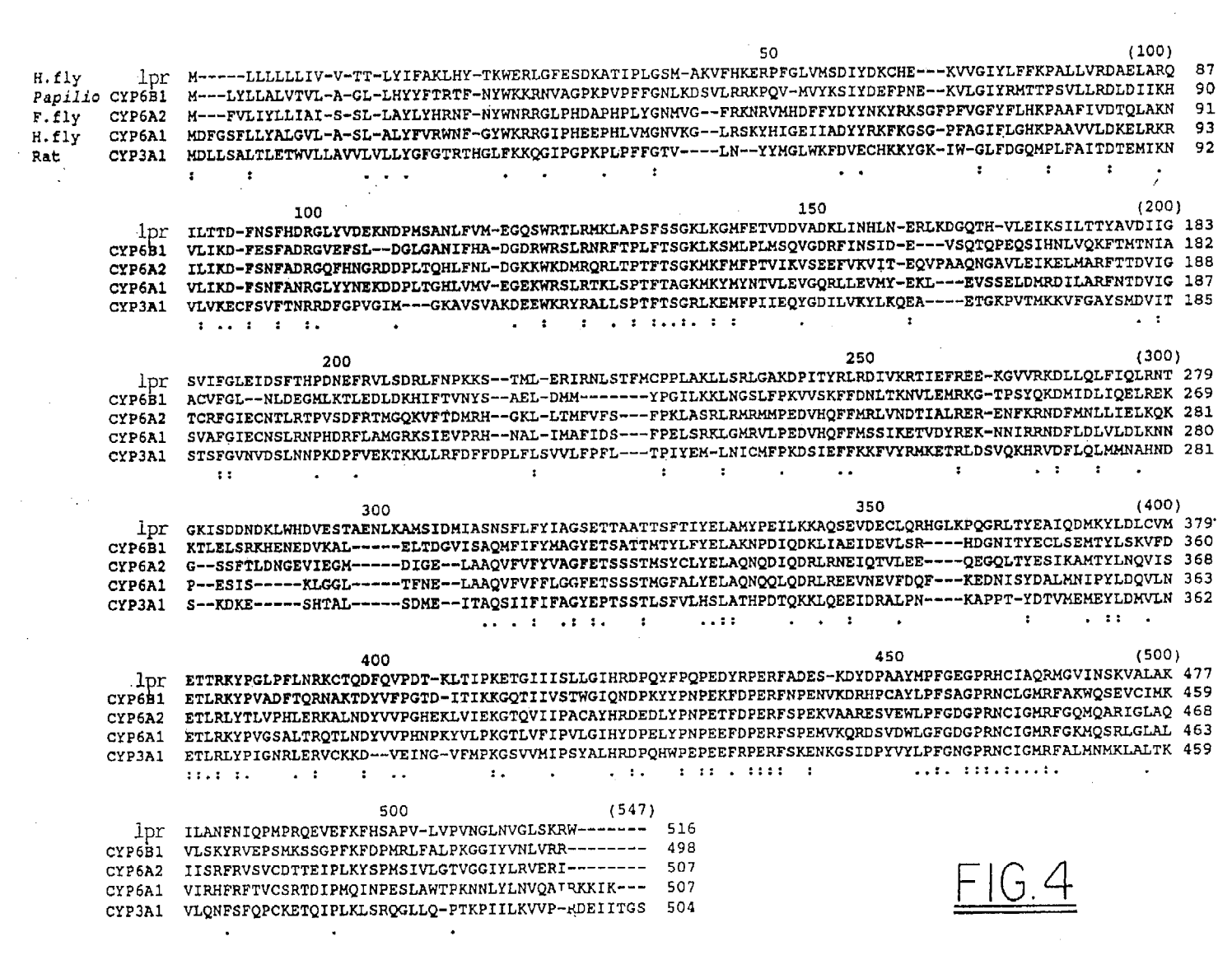

The P450$_{lpr}$ exhibits the greatest regional similarity index with *Drosophila melanogaster* CYP6A2 and black swallow-tail butterfly (*Papilio polyxenes*) CYP6B1, and also exhibits a high index with housefly CYP6A1 as well as with P450III family mammalian proteins. To close up conserved amino acids in cytochrome P450$_{lpr}$, an alignment was made with the cytochrome P450$_{lpr}$ and its similar 4 most similar sequences including the above 3 insect proteins and rat pcn1 (CYP3A1) (FIG. 4). First, multiple alignment among cytochrome P450$_{lpr}$ (SEQ. ID. No. 2), 6A1 (SEQ. ID. No. 22), 6A2 (SEQ. ID. No. 23), and 6B1 (SEQ. ID. No. 24) was made. This alignment was then overlaid onto the pcn1 sequence. The obtained alignment had identical residues and the residues shared among 4 sequences at 59 and 60 positions, respectively (FIG. 4). Based on this alignment, positional identity is presented in Table 2 using a total alignment window (positions 1–547).

TABLE 2

Percent Amino Acid Identity of P450s in Multiple Alignment

|  |  | pcn1 | 6A1 | 6A2 | 6B1 | lpr |
|---|---|---|---|---|---|---|
| Rat | pcn1 | — | 30.7 | 25.2 | 23.8 | 21.4 |
| H.fly | 6A1 | 30.5 | — | 37.8 | 27.1 | 23.8 |
| F.fly | 6A2 | 26.0 | 38.3 | — | 30.0 | 21.2 |
| Butterfly | 6B1 | 23.9 | 26.8 | 30.1 | — | 26.3 |
| H.fly | P450$_{lpr}$ | 21.9 | 24.5 | 21.7 | 27.0 | — |

The values in the upper right and lower left columns are based on a total alignment window (alignment positions 1–547) and a partial alignment window (33–547), respectively.

Amino acid identity of cytochrome P450$_{lpr}$ is 26.3, 23.8, 21.4, and 21.2% with 6B1, 6A1, pcn1 (CYP3A1) (SEQ. ID. No. 25), and 6A2, respectively. Higher identities are presented in sequence pairs of 6A1 and 6A2 (37.8%), 6A1 and pcn1 (30.7%), and 6A2 and 6B1 (30.0%). Also amino acid identity was calculated based on a partial alignment window (positions 33–547) to eliminate vulnerable alignment within the N-terminal region due to repetitive appearance of hydrophobic residues such as neu, although similarity tendency was essentially the same as the above results (Table 2). The hydrophobicity profile was quite similar among these 5 sequences, suggesting similarity in higher order structure among them.

The housefly P450$_{lpr}$ has several typical conserved regions as a microsomal P450 protein, as well as heme-binding region and highly hydrophobic N-terminal region. Possible functional regions in P450$_{lpr}$ are revealed in connection with the alignment from its most similar sequences (FIG. 4). (i) The invariant charged residues of Glu-380 and Arg-383 in lpr are involved in Helix K region in P450 cam. Tyl-373 in lpr is also conserved among animal P450s together with an alternate Leu at this position, while lpr and members of P450 family VI and III present variable residues at the lpr Leu-376 position instead of conserved Ala.

A typical sequence of P450 aromatic region appears with 2 invariant Pro residues and 3 aromatic residues within FXXPXXYXPXRF (SEQ. ID. No. 26) frame (residues 428–439) in lpr. In any SEQ. ID. No. 26, X is any amino acid. Phe-439 in this frame is a characteristic residue within microsomal P450s. Involvement of Helix K and aromatic regions in interaction with an electron-donor protein by intermolecular ion-pairing has been suggested.

Positions 126, 392, and 459 in cytochrome P450$_{lpr}$ are occupied by basic residues Arg. Conserved basic residues at these positions in animal P450s as well as P450cam may form ion pairs with heme propionate to incorporate essentially the same tertiary structure as P450cam. Thr-322 in cytochrome P450$_{lpr}$ appears to be an invariant residue. The Helix I region in P450cam involves this residue and may play a crucial role in catalytic function when in contact with the heme surface to bind oxygen and substrate molecules. A conserved acidic position just N-proximal to this Thr (Glu-321 in lpr) may form an internal ion pair with a basic residue located in the highly variable region. A basic residue Lys-343 and an acidic residue Asp-349 surrounding highly conserved Glu-347 in cytochrome P450$_{lpr}$ agree with a conserved charged frame among microsomal P450s. The corresponding Glu in P450cam is involved in Helix J region. This region can be incorporated together with Helix K region in the specific intermolecular interaction with a component of the electron-transfer system.

P450$_{lpr}$ protein sequence exhibits similarity to the members of P450 family VI and III. Lpr specifically catalyses pyrethroid insecticides with phenoxybenzyl alcohol moiety. Black swallow tail CYP6B1 presenting the highest similarity (26.2%) to cytochrome P450$_{lpr}$ metabolizes xanthotoxin in plant feeding of caterpillar. See Cohen, et al., M. Cohen, et al., "A Host-Inducable Cytochrome P450 from a Host Specific Caterpillar Molecule Cloning and Evolution," *Proc. Nat. Acad. Sci. USA*, 89:10920–24 (1992). Housefly 6A1 and *D. melanogaster* 6A2 are involved in detoxification of DDT and organophosphate insecticides, respectively, by their elevated expression in each resistant strain. See J. G. Scott, "The Cytochrome P450 Microsomal Monooxygenases of Insects: Recent Advances," *Rev. Pestic. Toxicol.*, Vol. 2, R. M. Roe et. al., editors (1993), which is hereby incorporated by reference. Rat pcn1 selectively metabolizes testosterone. It is elusive to correlate the protein structures with specific metabolic roles to date. Comparison of cytochrome P450$_{lpr}$ sequence with its similar 4 sequences reveals apparently excessive stretches in cytochrome P450$_{lpr}$ within the residues 169–163, 218–228, 295–307, and 355–360 (FIG. 4), and it is difficult to achieve alignment around these stretches. Two of them (residues 218–228 and 295–307) correspond to hyper variable domains in P450 supergene family members; the former stretch corresponds to a substrate binding region (spanning 175–207) of P450cam; and the latter corresponds to a postulated substrate binding region in mammalian P450s which can be localized in N-proximal to a substrate binding residue (within 243–252) of P450cam. Whether there are essential residues or local arrangements responsible for specific catalytic reactions in these stretches remains to be elucidated.

Three intron sequences were found from the coding region in cytochrome P450$_{lpr}$ genomic DNA, and they are inserted at sites within the corresponding codons of Thr-176, Glu-380, and Ala-463 (FIG. 2). The cytochrome P450$_{lpr}$ intron sites were compared with rat c (CYP1A1), rat b (CYP2A1), human scc (CYP11A1), and human c21b (CYP21A2) genes. Each of the mammalian genes was picked up as a representative member of the P450 family in which the gene structure is known. The codons corresponding to lpr intron insertion sites are Val-196, Glu-377, and Glu-463 in rat c genes. These positions are apparently different from that involved in the 4 mammalian genes described above. It seems difficult to explain a postulated idea that P450 gene families have diverged with deleting the introns involved in an ancestral gene sequence. Unfortunately, no other intron information is available from most similar P450III members and P450VI insect members to date, although an intron is not involved in Drosophila CYP6A2 gene structure. Evolutionary relationships among lpr and other barely similar P450s might be clarified from further intron information.

With the obtained cytochrome P450$_{lpr}$ cDNA sequence, there are several themes to be investigated in relation with genetic mechanism of elevated pyrethroid detoxification activity of lpr in insecticide resistant flies. First, is catalytic change in the molecule responsible for elevated detoxification of pyrethroids? As introduced, microsomes from pyrethroid resistant LPR strain of flies specifically detoxify deltamethrin. Several genetic polymorphisms responsible for amino acid substitution are identified in cDNA sequences from LPR and a susceptible strain. Second, whether an elevated expression of lpr is due to a difference in the copy number of the structure gene or transcriptional regulation. Cytochrome P450$_{lpr}$ protein is considerably overproduced in LPR flies. Esterase gene amplifications involved in organophosphate resistance in aphid and mosquito (J. G. Scott, "Insecticide Resistance in Insects," *Handbook of Pest Management*, P. Pimentel (ed.), CRC Press, pp. 663–77 (1991) have been well exemplified cases as the former possibility. However, in the case of cytochrome P450$_{lpr}$ overproduction in the LPR strain, at least the latter genetic mechanism should be working. Chromosomal linkage of the cytochrome P450$_{lpr}$ gene is already determined using the internal gene sequence polymorphism; the genetic factors which remarkably elevate the level of cytochrome P450$_{lpr}$ protein expression is localized not only within the same linkage as the cytochrome P450$_{lpr}$ gene but also in another chromosome by an immunoquantification assay. Thirdly, the DNA element and the factor which explains the difference in genetic inducibility of cytochrome P450$_{lpr}$ gene must be investigated. Interestingly, the cytochrome P450$_{lpr}$ proteins in insecticide susceptible stains is effectively inducible by phenobarbital with adult flies, while the cytochrome P450$_{lpr}$ protein in LPR strain is constitutively expressed over adult ages and the same induction treatment is not effective. See J. G. Scott, "The Cytochrome P450 Microsomal Monooxygenases of Insects: Recent Advances," *Rev. Pestic. Toxicol.*, Vol. 2, R. M. Roe et. al., editors (1993).

Example 11

Comparison with Nucleotide and Amino Acid Sequences for CYP6D1 Allele for Susceptible Flies The nucleotide sequence and deduced amino acid sequence for CS strain house flies susceptible to insecticides was determined in substantially the same way as described in Examples 2–9, starting with susceptible flies. The nucleotide sequence for susceptible house flies (SEQ. ID. No. 27) is:

```
ATGTTGTTATTACTGCTACTGATTGTGGTGACGACCCTCTACATCTTTGCCAAACTTCAT

TATACGAAATGGGAACGTTTGGGTTTCGAATCGGATAAGGCCACCATACCCCTGGGATCG

ATGGCAAAGGTGTTCCACAAGGAACGGCCATTTGGCCTGGTTATGTCCGACATATATGAC

AAATGCCACGAGAAGGTGGTGGGCATTTATTTGTTCTTCAAGCCGGCCCTACTGGTGCGC

GATGCCGAATTGGCGAGACAAATTTTGACCACGGATTTTAATAGCTTCCATGATCGTGGC

CTCTATGTGGATGAGAAAAATGATCCAATGTCGGCGAATCTTTTCGTGATGGAGGGTCAA

TCATGGCGTACGCTGAGAATGAAATTGGCCCCCTCGTTTTCGTCGGGTAAACTCAAGGGG

ATGTTCGAAACGGTCGATGATGTGGCGGATAAATTAATAAATCACTTGAATGAGCGCTTG

AAGGATGGCCAGACGCATGTTTTGGAAATCAAGAGTATTTTGACCACCTATGCTGTCGAC

ATCATTGGTTCGGTGATATTCGGCCTGGAAATCGATAGTTTCACCCATCCGGACAATGAA

TTTCGTGTCTTGAGTGATCGTCTATTTAACCCAAAGAAGTCGACAATGTTGGAGAGATTT

CGCAATTTATCAACCTTTATGTGTCCACCACTTGCCAAACTCTTGTCGCGCCTTGGTGCC

AAGGATCCGATAACATATCGCCTGCGCGACATCGTGAAACGGACGATAGAATTTCGCGAA

GAAAAGGGCGTTGTACGCAAAGATCTTCTCCAGCTATTTATACAACTCAGAAATACTGGT
```

AAAATTTCCGATGACAACGACAAGCTATGGCATGACGTTGAGTCGACGGCGGAAAATCTC

AAAGCCATGTCCATCGATATGATTGCCTCCAATTCATTCTTATTCTATATTGCCGGATCG

GAAACAACGGCGGCCACAACATCATTTACCATCTATGAATTGGCCATGTATCCGGAAATT

CTGAAGAAGGCCCAAAGCGAGGTGGATGAGTGTCTGCAAAGGCACGGTCTCAAGCCGCAG

GGACGGCTGACCTATGAGGCCATACAGGATATGAAATATTTGGATTTGTGTGTTATGGAA

ACCACCCGCAAATACCCTGGCCTGCCGTTTTGAATCGCAAATGCACTCAGGATTTCCAA

GTACCCGACACAAAACTTACCATACCCAAGGAAACGGGAATTATCATCTCCCTCTTGGGC

ATCCATAGAGACCCACAGTATTTCCCCCAACCCGAGGATTATAGGCCAGAACGCTTTGCC

GATGAGAGCAAGGATTATGATCCAGCGGCATATATGCCTTTTGGAGAGGGTCCAAGGCAC

TGTATTGCTCAACGCATGGGCGTTATGAATTCCAAGGTAGCCTTGGCCAAAATATTGGCC

AATTTTAATATTCAACCAATGCCCCGCCAAGAAGTTGAGTTCAAATTCCATTCAGCTCCT

GTTCTGGTACCAGTAAATGGTCTCAATGTGGGTCTATCGAAGAGGTGGTGA

The amino acid sequence (SEQ. ID. No. 28) for susceptible house flies is:

| Met | Leu | Leu | Leu | Leu | Leu | Leu | Ile | Val | Val |
|---|---|---|---|---|---|---|---|---|---|
| Thr | Thr | Leu | Tyr | Ile | Phe | Ala | Lys | Leu | His |
| Tyr | Thr | Lys | Trp | Glu | Arg | Leu | Gly | Phe | Glu |
| Ser | Asp | Lys | Ala | Thr | Ile | Pro | Leu | Gly | Ser |
| Met | Ala | Lys | Val | Phe | His | Lys | Glu | Arg | Pro |
| Phe | Gly | Leu | Val | Met | Ser | Asp | Ile | Tyr | Asp |
| Lys | Cys | His | Glu | Lys | Val | Val | Gly | Ile | Tyr |
| Leu | Phe | Phe | Lys | Pro | Ala | Leu | Leu | Val | Arg |
| Asp | Ala | Glu | Leu | Ala | Arg | Gln | Ile | Leu | Thr |
| Thr | Asp | Phe | Asn | Ser | Phe | His | Asp | Arg | Gly |
| Leu | Tyr | Val | Asp | Glu | Lys | Asn | Asp | Pro | Met |
| Ser | Ala | Asn | Leu | Phe | Val | Met | Glu | Gly | Gln |
| Ser | Trp | Arg | Thr | Leu | Arg | Met | Lys | Leu | Ala |
| Pro | Ser | Phe | Ser | Ser | Gly | Lys | Leu | Lys | Gly |
| Met | Phe | Glu | Thr | Val | Asp | Asp | Val | Ala | Asp |
| Lys | Leu | Ile | Asn | His | Leu | Asn | Glu | Arg | Leu |
| Lys | Asp | Gly | Gln | Thr | His | Val | Leu | Glu | Ile |
| Lys | Ser | Ile | Leu | Thr | Thr | Tyr | Ala | Val | Asp |
| Ile | Ile | Gly | Ser | Val | Ile | Phe | Gly | Leu | Glu |
| Ile | Asp | Ser | Phe | Thr | His | Pro | Asp | Asn | Glu |
| Phe | Arg | Val | Leu | Ser | Asp | Arg | Leu | Phe | Asn |
| Pro | Lys | Lys | Ser | Thr | Met | Leu | Glu | Arg | Phe |
| Arg | Asn | Leu | Ser | Thr | Phe | Met | Cys | Pro | Pro |
| Leu | Ala | Lys | Leu | Leu | Ser | Arg | Leu | Gly | Ala |
| Lys | Asp | Pro | Ile | Thr | Tyr | Arg | Leu | Arg | Asp |
| Ile | Val | Lys | Arg | Thr | Ile | Glu | Phe | Arg | Glu |
| Glu | Lys | Gly | Val | Val | Arg | Lys | Asp | Leu | Leu |
| Gln | Leu | Phe | Ile | Gln | Leu | Arg | Asn | Thr | Gly |
| Lys | Ile | Ser | Asp | Asp | Asn | Asp | Lys | Leu | Trp |
| His | Asp | Val | Glu | Ser | Thr | Ala | Glu | Asn | Leu |
| Lys | Ala | Met | Ser | Ile | Asp | Met | Ile | Ala | Ser |
| Asn | Ser | Phe | Leu | Phe | Tyr | Ile | Ala | Gly | Ser |
| Glu | Thr | Thr | Ala | Ala | Thr | Thr | Ser | Phe | Thr |
| Ile | Tyr | Glu | Leu | Ala | Met | Tyr | Pro | Glu | Ile |
| Leu | Lys | Lys | Ala | Gln | Ser | Glu | Val | Asp | Glu |
| Cys | Leu | Gln | Arg | His | Gly | Leu | Lys | Pro | Gln |
| Gly | Arg | Leu | Thr | Tyr | Glu | Ala | Ile | Gln | Asp |
| Met | Lys | Tyr | Leu | Asp | Leu | Cys | Val | Met | Glu |
| Thr | Thr | Arg | Lys | Tyr | Pro | Gly | Leu | Pro | Phe |

-continued

| Leu | Asn | Arg | Lys | Cys | Thr | Gln | Asp | Phe | Gln |
|---|---|---|---|---|---|---|---|---|---|
| Val | Pro | Asp | Thr | Lys | Leu | Thr | Ile | Pro | Lys |
| Glu | Thr | Gly | Ile | Ile | Ile | Ser | Leu | Leu | Gly |
| Ile | His | Thr | His | Pro | Gln | Tyr | Phe | Pro | Gln |
| Pro | Glu | Asp | Tyr | Arg | Pro | Glu | Arg | Phe | Ala |
| Asp | Glu | Ser | Lys | Asp | Tyr | Asp | Pro | Ala | Ala |
| Tyr | Met | Pro | Phe | Gly | Glu | Gly | Pro | Arg | His |
| Cys | Ile | Ala | Gln | Arg | Met | Gly | Val | Met | Asn |
| Ser | Lys | Val | Ala | Leu | Ala | Lys | Ile | Leu | Ala |
| Asn | Phe | Asn | Ile | Gln | Pro | Met | Pro | Arg | Gln |
| Glu | Val | Glu | Phe | Lys | Phe | His | Ser | Ala | Pro |
| Val | Leu | Val | Pro | Val | Asn | Gly | Leu | Asn | Val |
| Gly | Leu | Ser | Lys | Arg | Trp | TGA | | | |

As shown in FIG. 5, a comparison of the amino acid sequence for cytochrome P450$_{lpr}$ (SEQ. ID. No. 2), identified as LPR in FIG. 5, and the corresponding amino acid sequence for susceptible house flies (SEQ. ID. No. 28), identified as CS in FIG. 5, demonstrates that these sequences are substantially similar except that amino acid 220 is isoleucine in the former and phenylalanine in the latter, while amino acid 469 is isoleucine in the former and methionine in the latter. These differences are highlighted by enclosure in rectangles in FIG. 5. In FIGS. 6A–D, a comparison of the nucleotide sequence for cytochrome P450$_{lpr}$ (SEQ. ID. No. 1), identified as LPR in FIGS. 6A–D, and the corresponding nucleotide sequence for susceptible house flies (SEQ. ID. No. 29), identified as CS in FIGS. 6A–D, is made. This demonstrates that there are a number of differences in the nucleotides even though most of these differences do not change the encoded amino acids. The two underlined nucleotides in FIGS. 6A–D are the only differences between the CS allele and LPR allele that result in amino acid changes in the protein. Whether or not the change in the two amino acids between CS and LPR alters the catalytic activity of the protein is unknown.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated DNA molecule encoding cytochrome P450$_{lpr}$ polypeptide, wherein said DNA molecule is either the nucleotide sequence of SEQ. ID. NO. 1 or DNA variants of said sequence which retain cytochrome P450$_{lpr}$ dependent enzymatic activity.

2. An isolated DNA molecule according to claim 1, wherein said DNA molecule has a nucleotide sequence of SEQ. ID. No. 1.

3. An expression system comprising the isolated DNA molecule of claim 1 in a vector heterologous to the DNA molecule.

4. An expression system according to claim 3, wherein the DNA molecule is inserted into the vector in proper sense orientation and correct reading frame.

5. An expression system according to claim 3, wherein the vector is a baculovirus vector.

6. An expression system according to claim 3, wherein the DNA molecule has a nucleotide sequence of SEQ. ID. No. 1.

7. A cell transformed with a heterologous DNA molecule encoding cytochrome P450$_{lpr}$, wherein said heterologous DNA molecule is either the nucleotide sequence of SEQ. ID. NO. 1 or DNA variants of said sequence which retain cytochrome P450$_{lpr}$ dependent enzymatic activity.

8. A cell according to claim 7, wherein the DNA molecule has a nucleotide sequence of SEQ. ID. No. 1.

9. A cell according to claim 7, wherein the DNA molecule is inserted into a heterologous expression system.

10. A cell according to claim 7, wherein the cell is selected from the group consisting of plant cells, mammalian cells, insect cells, and bacterial cells.

11. A method of adult insect control comprising: treating adult insects with a vector comprising the DNA molecule of claim 6 together with an organophosphate insecticide.

12. A method according to claim 11, wherein said DNA molecule has a nucleotide sequence of SEQ. ID. No. 1.

13. A method according to claim 11, wherein the vector is a baculovirus vector.

14. A method according to claim 11, wherein said treating is carried out by spraying the vector on adult insects.

15. A method according to claim 11, wherein the vector is applied to a surface together with an attractant during said treating.

16. A transgenic plant transformed with the DNA molecule of claim 1.

17. A transgenic plant according to claim 16, wherein the DNA molecule has a nucleotide sequence of SEQ. ID. No. 1.

18. A transgenic plant according to claim 16, wherein the transgenic plant is a crop plant selected from the group consisting of dicots and monocots.

* * * * *